US009539118B2

(12) United States Patent
Leuthardt et al.

(10) Patent No.: US 9,539,118 B2
(45) Date of Patent: Jan. 10, 2017

(54) BRAIN-CONTROLLED BODY MOVEMENT ASSISTANCE DEVICES AND METHODS

(71) Applicant: Neurolutions, Inc., St Louis, MO (US)

(72) Inventors: Eric C. Leuthardt, St. Louis, MO (US); Lonnie J. Love, St Louis, MO (US); Rob Coker, St Louis, MO (US); Daniel W. Moran, Ballwin, MO (US)

(73) Assignee: Neurolutions, Inc., Clayton, MO (US)

( * ) Notice: Subject to any disclaimer, the term of this patent is extended or adjusted under 35 U.S.C. 154(b) by 732 days.

(21) Appl. No.: 13/842,749

(22) Filed: Mar. 15, 2013

(65) Prior Publication Data

US 2014/0277582 A1    Sep. 18, 2014

(51) Int. Cl.
| | | |
|---|---|---|
| A61F 2/72 | (2006.01) | |
| A61H 1/02 | (2006.01) | |
| A61B 5/0476 | (2006.01) | |
| A61F 2/54 | (2006.01) | |
| A61F 2/68 | (2006.01) | |

(52) U.S. Cl.
CPC .............. *A61F 2/72* (2013.01); *A61B 5/0476* (2013.01); *A61B 2505/09* (2013.01); *A61F 2/54* (2013.01); *A61F 2002/6827* (2013.01); *A61H 1/0288* (2013.01); *A61H 2230/10* (2013.01)

(58) Field of Classification Search
CPC ...... A61F 2/54; A61F 2/72; A61F 2002/6827; A61B 5/0476; A61B 2505/09; A61H 1/0255; A61H 2230/10
See application file for complete search history.

(56) References Cited

U.S. PATENT DOCUMENTS

| | | |
|---|---|---|
| 5,638,826 A | 6/1997 | Wolpaw et al. |
| 7,058,445 B2 | 6/2006 | Kemere et al. |
| 7,120,486 B2 | 10/2006 | Leuthardt et al. |

(Continued)

FOREIGN PATENT DOCUMENTS

| | | |
|---|---|---|
| WO | WO 2005/074369 | 8/2005 |
| WO | WO 2005/074370 | 8/2005 |

(Continued)

OTHER PUBLICATIONS

"Combination Neuromuscular Electrical Stimulator, Interferential Stimulator, and Transcutaneous Electrical Nerve Stimulator, Model NexWare," 510(k) No. K111279 [letter, indications for use], Sep. 2011, 3 pages.

(Continued)

*Primary Examiner* — Quang D Thanh
(74) *Attorney, Agent, or Firm* — Fish & Richardson P.C.

(57) ABSTRACT

Methods, devices, systems, and apparatus, including computer programs encoded on a computer storage medium, for brain-controlled body movement assistance devices. In one aspect, a device includes a brain-controlled body movement assistance device with a brain-computer interface (BCI) component adapted to be mounted to a user, a body movement assistance component operably connected to the BCI component and adapted to be worn by the user, and a feedback mechanism provided in connection with at least one of the BCI component and the body movement assistance component, the feedback mechanism being configured to output information relating to a usage session of the brain-controlled body movement assistance device.

16 Claims, 16 Drawing Sheets

(56) References Cited

U.S. PATENT DOCUMENTS

| | | | |
|---|---|---|---|
| 7,826,894 | B2 | 11/2010 | Masallam et al. |
| 8,165,685 | B1 | 4/2012 | Knutson et al. |
| 8,177,732 | B2 | 5/2012 | Einav et al. |
| 8,214,029 | B2 | 7/2012 | Koeneman et al. |
| 8,938,289 | B2 | 1/2015 | Einav et al. |
| 2005/0131311 | A1 | 6/2005 | Leuthardt et al. |
| 2006/0167371 | A1* | 7/2006 | Flaherty ............... A61F 2/50 600/545 |
| 2006/0173259 | A1 | 8/2006 | Flaherty et al. |
| 2006/0293617 | A1 | 12/2006 | Einav et al. |
| 2009/0099627 | A1* | 4/2009 | Molnar ............ A61B 5/04014 607/62 |
| 2009/0221928 | A1* | 9/2009 | Einav ................ A61B 5/0484 600/544 |
| 2009/0306531 | A1 | 12/2009 | Leuthardt et al. |
| 2010/0094154 | A1 | 4/2010 | Schalk et al. |
| 2011/0009788 | A1 | 1/2011 | Kelly et al. |
| 2011/0295338 | A1 | 12/2011 | Rickert et al. |
| 2011/0307079 | A1* | 12/2011 | Oweiss .............. A61B 5/048 623/27 |
| 2012/0052905 | A1* | 3/2012 | Lim .................... G06F 3/015 455/550.1 |

FOREIGN PATENT DOCUMENTS

| | | |
|---|---|---|
| WO | WO 2005/074373 | 8/2005 |
| WO | WO 2005/075155 | 8/2005 |
| WO | WO 2005/086574 | 9/2005 |
| WO | WO 2005/087307 | 9/2005 |
| WO | WO 2005/105203 | 11/2005 |
| WO | WO 2011/123072 | 10/2011 |

OTHER PUBLICATIONS

"Encephalogram Telemetry System," Product Classification—FDA [online] [retrieved on Jan. 31, 2012] Retrieved from the Internet: <URL: http://www.accessdata.fda.gov/scripts/cdrh/cfdocs/cfPCD/classification.cfm?ID=3230>, 1 page.

"Mentor Hand Therapy Device," FDA [online] [retrieved on Jan. 31, 2012], retrieved from the Internet: <URL: http://www.accessdata.fda.gov/scripts/cdrh/cfdocs/cfRL/LDetails.cfm?LID=81677>, 3 pages.

Bally et al., "Effects of the SaeboFlex® Orthosis and a home exercise program on upper extremity recovery in individuals with chronic," *J. Neuro Phys Thera*, 30(4):207, Dec. 2006.

Biomove 3000 System 510(k) No. K042650, [summary, letter, indications for use] dated Jan. 2005, 6 pages.

Biomove 5000 System 510(k) No. K080787, [summary, letter, indications for use] dated Apr. 2008, 6 pages.

Bioness Inc., "Ness H2000® Wireless," [product brochure], 3 pages, copyright 2011.

BIS EEG VISTA Monitor System 510(k) No. K072286, [summary, letter, indications for use] dated Nov. 2007, 8 pages.

Buch et al, "Think to move: a neuromagnetic brain-computer interface (BCI) system for chronic stroke," *Stroke*, 39(3):910-917, print Mar. 2008, Epub Feb. 2008.

Cigna, "Cigna Medical Coverage Policy," Aug. 15, 2011, 41 pages.

Daly & Wolpaw, "Brain-computer interfaces in neurological rehabilitation," *Lancet Neurol.*, 7(11):1032-1043, Nov. 2008.

Fok et al., "An EEG-based Brain Computer Interface for Rehabilitation and Restoration of Hand Control following Stroke Using Ipsilateral Cortical Physiology," [senior design paper] ESE 498, Washington University in St. Louis, Retrieved from the Internet <URL: http://ese.wustl.edu/ContentFiles/Research/UndergraduateResearch/CompletedProjects/WebPages/sp11/SamRaphaelChuck/Senior%20Design%20Paper.pdf> 26 pages, Apr. 2011.

Fok et al., "IpsiHand: An EEG-based brain computer interface for rehabilitation and restoration of hand control following stroke and traumatic brain injury using Ipsilateral Cortical Physiology," [poster] Washington University in St. Louis, 1 page, Apr. 2011.

Fok et al., "IpsiHand: Direct Recoupling of Intention and Movement (Washington University in St. Louis)," RESNA Student Design Competition [online] Apr. 27, 2011 [retrieved on Jun. 17, 2013]. Retrieved from the Internet <URL: http://aac-rerc.psu.edu/wordpressmu/RESNA-SDC/2011/04/27/ipsihand-direct-recoupling-of-intention-and-movement-washington-university-in-st-louis/> 8 pages.

Harmonic System 510(k) No. K083577, [summary, letter, indications for use] dated Aug. 2011, 6 pages.

Holmes et al., "IpsiHand Bravo: an improved EEG-based brain-computer interface for hand motor control rehabilitation" *ConfProc IEEE Eng Med Biol Soc.* 2012:1749-1752, Aug. 28-Sep. 1, 2012.

Jones et al.. "Impairment and Recovery of Ipsilateral Sensory-Motor Function Following Unilateral Cerebral Infarction" *Brain*, 112: 113-132, 1989.

L300 Plus System (Right, Left), L300 Plus System Upgrade Kit (Right, Left), Devices@FDA [online] Apr. 2011 [retrieved on Jan. 31, 2012]. Retrieved from the Internet: <URL: http://www.accessdata.fda.gov/SCRIPTs/cdrh/devicesatfda/index.cfm?db=pmn&id=K103>, 1 page.

Leuthardt et al., "The emerging world of motor neuroprosthetics: a neurosurgical perspective," *Neurosurgery*, 59(1):1-14, Jul. 2006.

Maude Adverse Event Report, "Bioness Bioness, Bioness H200 4.5 AMPS," FDA [online] Jan. 21, 2011 [retrieved on Jan. 31, 2012] Retrieved from the Internet: <URL: http://www.accessdata.fda.gov/scripts/cdrh/cfdocs/cfmaude/detail.cfm?mdrfoi_id=2023489>, 1 page.

Mehring et al., "Comparing information about arm movement direction in single channels of local and epicortical field potentials from monkey and human motor cortex", *Journal of Physiology—Paris*, 98:498-506, 2004.

Meng et al., "BCI-FES training system design and implementation for rehabilitation of stroke patients," in 2008 International Joint Conference on Neural Networks (IJCNN 2008), pp. 4103-4106, Jun. 1-8, 2008.

mPower 100 EMG Sensor, FDA [online]retrieved on Jan. 31, 2012]. Retrieved from the Internet: <URL: http://www.accessdata.fda.gov/scripts/cdrh/cfdocs/cfRL/LDetail.cfm?LID=226356>, 1 page.

mPower 1000, Orthosis, Limb Brace, FDA [online] retrieved on Jan. 31, 2012]. Retrieved from the Internet: <URL: http://www.accessdata.fda.gov/scripts/cdrh/cfdocs/cfRL/LDetails.cfm?LID=220937>, 1 page.

Myomo e 100, 510(k) No. K062631, [summary, letter, indications for use] dated Apr. 2007, 7 pages.

NESS L300 510(k) No. K080219, [summary, letter, indications for use] dated Jan. 2008, 5 pages.

NESS L300 Plus system 510(k) No. K103343, [summary, letter, indications for use] dated Apr. 2011, 8 pages.

OmniPro™ System, 510(k) No. K050143, [summary, letter, indications for use] dated Feb. 2005, 7 pages.

Porro et al., "Ipsilateral involvement of primary motor cortex during motor imagery," *Eur J Neurosci.*, 12(8):3059-3063, Aug. 2000.

Prasad et al., "Using motor imagery based brain-computer interface for post-stroke rehabilitation," *Proceedings of the 4th International IEEE/EMBS Conference on Neural Engineering*, pp. 258, 262, Antalya, Turkey, Apr. 29-May 2, 2009.

Regence Medical Policy, "Functional Neuromuscular Electrical Stimulation," Jul. 2000, 8 pages.

Saebo Arm Training Program, *Saebo*Reach ®, *Saebo*Flex®, *Saebo*Stretch®, *Seaebo*Glide®, [product brochure], 8 pages, created Jun. 2008.

SaeboFlex; Saebostetch, FDA [online] retrieved on Jan. 1, 2012. Retrieved from the Internet: <URL: http://www.accessdata.fda.gov/scripts/cdrh/cfdocs/cfRL/LDetails.cfm?LID=99358 >, 2 pages.

Schalk, "BCI2000: a general-purpose brain-computer interface (BCI) system," *IEEE Trans Biomed Eng.* 51(6):1034-1043, Jun. 2004.

Univerisity of Missouri—Columbia, "Bilateral Versus Unilateral Task Retraining Using the SaeboFlex Orthosis," ClinicalTrials.gov

(56) References Cited

OTHER PUBLICATIONS

[online] Feb. 28, 2011 [retrieved on Jan. 14, 2012] Retrieved from the Internet: <URL: http://clinicaltrials.gov/ct2/show/NCT00893776>, 4 pages.

Wang et al., "A feasibility study of non-invasive motor-imagery BCI-based robotic rehabilitation for stroke patients," *Proceedings of the 4th International IEEE/EMBS Conference on Neural Engineering*, pp. 271-274, Antalya, Turkey, Apr. 29-May 2, 2009.

Wisneski et al., "Unique cortical physiology associated with ipsilateral hand movements and neuroprosthetic implications," *Stroke*, 39(12):3351-3359, print Dec. 2008, Epub Oct. 2008.

International Preliminary Report on Patentability and Written Opinion for PCT/US2008/065953, issued Dec. 7, 2009, 6 pages.

International Search Report for PCT/US2008/065953, mailed Oct. 1, 2008, 1 page.

European Supplementary Search Report for Application No. 14767543.3, dated Nov. 7, 2016, 6 pages.

\* cited by examiner

BRAIN-CONTROLLED BODY MOVEMENT ASSISTANCE DEVICES AND METHODS

STATEMENT OF FEDERAL GOVERNMENT RIGHTS

This invention was made with government support under Work for Others Agreement No. NFE-15-05518, between UT-Battelle, LLC, operating under Prime Contract No. DE-AC05-00OR22725 for the U.S. Department of Energy, and Neurolutions, Inc. The government has certain rights in the invention.

This specification relates to brain-controlled devices and methods and related equipment that assist users in performing body movements.

BACKGROUND

Brain-computer interface (BCI) technology involves the acquisition and interpretation of brain signals to determine the intentions of the person that produced the brain signals, and then using the determined intentions to carry out intended tasks. One example application of BCI technologies is the control of a cursor on a computer screen. There are many others.

Another example application area for BCI technologies is in connection with stroke patients. Unilateral stroke, for example, is a stroke event that affects only, or mainly, one side of the brain. When a unilateral stroke occurs, the opposite side of the stoke victim's body may be left paralyzed or weak. That is because in normal function, one side or hemisphere of the brain controls the opposite, or contralateral, side of the body. Thus, the right brain, or right cerebral hemisphere, controls the left side of the body, and vice-versa.

Patients who have experienced a brain injury (e.g., stroke, trauma, infection, hemorrhage, neonatal malformation, cerebral palsy, or neurodegenerative) typically undergo some type of rehabilitation in an attempt to restore or strengthen the motor impaired or paralyzed side of the body, often using a variety of rehabilitation devices that aid in the rehabilitation effort. Often, the rehabilitation method involves equipment that requires the patient, in order to perform the necessary rehabilitation activities, to be at a particular location such as a rehabilitation facility where the equipment is located.

The present inventors believe that such constraints often negatively impact the potential for success in the rehabilitation effort for a variety of reasons. For example, use of rehabilitation equipment at a rehabilitation facility can cause the rehabilitation to be performed outside of the context of the patient's domestic needs (e.g., performing daily activities at the patient's home) and can cause the rehabilitation to be limited to specific amounts of time, both of which can limit progress made a patient during rehabilitation. Repetitions in the context of a patient's living environment with objects and surrounding from a patient's daily life can increase the effectiveness of rehabilitation activities. Rehabilitation using rehabilitation equipment that is removed from such a context (e.g., patient's home) and that is available for limited periods of time (e.g., scheduled appointments at rehabilitation facility) may not be optimized to provide the best recovery for a patient.

The use of BCI technology for stroke patient rehabilitation is described, for example, in U.S. patent application Ser. No. 12/133,919 to Leuthardt et al. ('919 application). The '919 application describes a BCI system to assist a hemiparetic subject, or in other words, a subject who has suffered a unilateral stroke brain insult and thus has an injury in, or mainly in, one hemisphere of the brain. For that patient, the other hemisphere of the brain may be normal. The '531 patent application describes an idea of ipsilateral control, in which brain signals from one side of the brain are used to control body functions on the same side of the body. The present inventors believe this idea of ipsilateral control is particularly useful in the context of unilateral stroke patients where, again, the opposite brain hemisphere may be damaged or impaired and thus may not produce useful brain signals for use by a BCI system.

SUMMARY

In one implementation, a brain-controlled body movement assistance device includes a brain-computer interface (BCI) component adapted to be mounted to a user, the BCI component configured to (i) receive brain signal information captured from the patient by a brain signal acquisition system, (ii) process the captured brain signal information to detect if the captured brain signal information is indicative of an intention by the patient related to one or more predefined movements of one or more of the user's body parts, and (iii) if an intention of one of the one or more predefined movements is detected, produce an output signal indicative of the detected predefined movement; a body movement assistance component operably connected to the BCI component and adapted to be worn by the user in proximity to and attached with the body parts of the one or more predefined movements, the body movement assistance component being configured to (i) receive from the BCI component an output signal of a detected predefined movement, and (ii) in response thereto, induce or assist in moving the one or more body parts in accordance with the detected predefined movement; and a feedback mechanism provided in connection with at least one of the BCI component and the body movement assistance component, the feedback mechanism being configured to output information relating to a usage session of the brain-controlled body movement assistance device.

Such a brain-controlled body movement assistance device may optionally include one or more of the following features. The feedback mechanism can include a display device that is positioned to enable the user to view the display device when the brain-controlled assistance device is mounted to the user, the display device further configured to display the information relating to the usage session of the brain-controlled assistance device. The feedback mechanism can include an audio output device that is configured to audibly output the information relating to the usage session of the brain-controlled assistance device. The brain-controlled body movement assistance device can further include one or more batteries that are electrically connected to the BCI component, to the body movement assistance component, and to the feedback mechanism, the one or more batteries being configured to store a charge and to provide electrical power to the BCI component, to the body movement assistance component, and to the feedback mechanism at least while the device is untethered from an external power source. The device can be wearable by the user and can be configured to be worn on top of a particular body part of the user through the use of one or more attachment mechanisms. The usage session of the brain-controlled body movement assistance device can include a rehabilitation session during which one or more rehabilitation exercises are performed by the body movement assistance component with regard to the particular body part based on captured brain signals that are determined by the BCI interface to indicate an intention to move the particular body part. The information output by the feedback mechanism can describe the detected intention to move the particular body part and the one or more rehabilitation exercises that are being performed by the body movement assistance component. The brain-controlled body movement assistance device can further include a prompt mechanism that is provided in connection with at least one of the BCI component and the body movement assistance component, the prompt mechanism being configured to generate one or more sensory stimulations to prompt the user to generate one or more particular brain signals.

In another implementation, a brain-controlled body movement assistance device includes a brain-computer interface (BCI) component adapted to be mounted to a user, the BCI component configured to (i) receive brain signal information captured from the patient by a brain signal acquisition system, (ii) process the captured brain signal information to detect if the captured brain signal information is indicative of an intention by the patient related to one or more predefined movements of one or more of the user's body parts, and (iii) if an intention of one of the one or more predefined movements is detected, produce an output signal indicative of the detected predefined movement; a body movement assistance component operably connected to the BCI component and adapted to be worn by the user in proximity to and attached with the body parts of the one or more predefined movements, the body movement assistance component being configured to (i) receive from the BCI component an output signal of a detected predefined movement, and (ii) in response thereto, induce or assist in moving the one or more body parts in accordance with the detected predefined movement; and a prompt mechanism that is provided in connection with at least one of the BCI component and the body movement assistance component, the prompt mechanism being configured to generate one or more sensory stimulations to prompt the user to generate one or more particular brain signals.

Such a brain-controlled body movement assistance device may optionally include one or more of the following features. The prompt mechanism can include a display device that is positioned to enable the user to view the display device when the brain-controlled assistance device is mounted to the user, the display device further configured to display information to prompt the user to generate the one or more particular brain signals. The prompt mechanism can include one or more tactile prompt interfaces that are configured to provide tactile stimulation to one or more portions of the user's body. The prompt mechanism can include one or more electrical stimulators that are configured to stimulate particular nerves or muscles of the users body through the application of electrical current at one or more locations on the user's body. The prompt mechanism can include an audio output device that is configured to audibly output information to prompt the user to generate the one or more particular brain signals.

In another implementation, a wearable brain-controlled device for rehabilitation of one or more brain injuries includes a brain-computer interface (BCI) component adapted to be worn on a forearm of a user, the BCI component configured to (i) receive brain signal information captured from the patient by a brain signal acquisition system, (ii) process the captured brain signal information to detect if the captured brain signal information is indicative of an intention by the patient related to one or more predefined movements of the user's hand, and (iii) if an intention of one of the one or more predefined movements is detected from the captured brain signal information, produce an output signal of the detected predefined movement; a hand movement assistance component operably connected to the BCI component and adapted to be worn by and connect to a hand of the user, the hand movement assistance component being configured to (i) receive from the BCI component an output signal of a detected predefined movement, and (ii) in response thereto, induce or assist in moving the hand in accordance with the detected predefined movement; and a display device provided on the BCI component and positioned to enable the user to view the display device when the BCI component is worn on the forearm of the user, the display device further configured to display information relating to a usage session of the brain-controlled wearable rehabilitation device.

Such a wearable brain-controlled device may optionally include one or more of the following features. The one or more brain injuries can include strokes that have impaired movement of the hand of the user to which the hand movement assistance component is connected. The hand of the user can be on a first side of the user's body, and the brain signal information that is processed and used to determine whether the user has demonstrated an intention to move the hand, can be captured from a side of the user's brain that is a same side of the user's body as the first side of the user's body. The usage session can include a rehabilitation session that includes opening and closing the user's impaired hand in response to detected brain signals.

In another implementation, a brain-controlled wearable rehabilitation device can include a brain-computer interface (BCI) component adapted to be worn on a forearm of a user, the BCI component configured to (i) receive brain signal information captured from the patient by a brain signal acquisition system, (ii) process the captured brain signal information to detect if the captured brain signal information is indicative of an intention by the patient related to one or more predefined movements of the user's hand, and (iii) if an intention of one of the one or more predefined movements is detected from the captured brain signal information, produce an output signal of the detected predefined movement; and a hand movement assistance component operably connected to the BCI component and adapted to be worn by and connect to a hand of the user, the hand movement assistance component being configured to (i) receive from the BCI component an output signal of a detected predefined movement, and (ii) in response thereto, induce or assist in moving the hand in accordance with the detected predefined movement, wherein the hand movement assistance component includes an extension member to which a finger attachment mechanism is slidably attached, the extension member being adapted to be moved in a first direction that is downward in relation to the top of an attached finger to provide flexion movement of the attached finger and adapted to be moved in an opposite, second direction that is upward in relation to the top of an attached finger to provide extension movement of the attached finger.

Such a brain-controlled wearable rehabilitation device may optionally include one or more of the following features. An attachment mechanism of the finger attachment mechanism to the extension member can be adapted to allow rocking of the finger attachment mechanism with respect to the extension member. The hand movement assistance component can further include a hinged thumb-support mechanism that is adapted to pivot on an axis defined by a hinge from i) a first position that supports and restrains a thumb of the hand of the user when the hand movement assistance component is connected to the hand of the user to ii) a second position that does not support or restrain the thumb.

BRIEF DESCRIPTION OF THE DRAWINGS

Like reference numbers and designations in the various drawings indicate like elements.

DETAILED DESCRIPTION

This specification generally describes brain-controlled devices and methods and related equipment that assist users in performing body movements. This technology may be particularly useful for stroke patients in their rehabilitation efforts to regain or improve motor functions affected by stroke events. While this stroke rehabilitation application of the present BCI technology will be described in this specification in detail, the techniques described in this specification have much broader applicability beyond stroke rehabilitation.

Figure 1A:
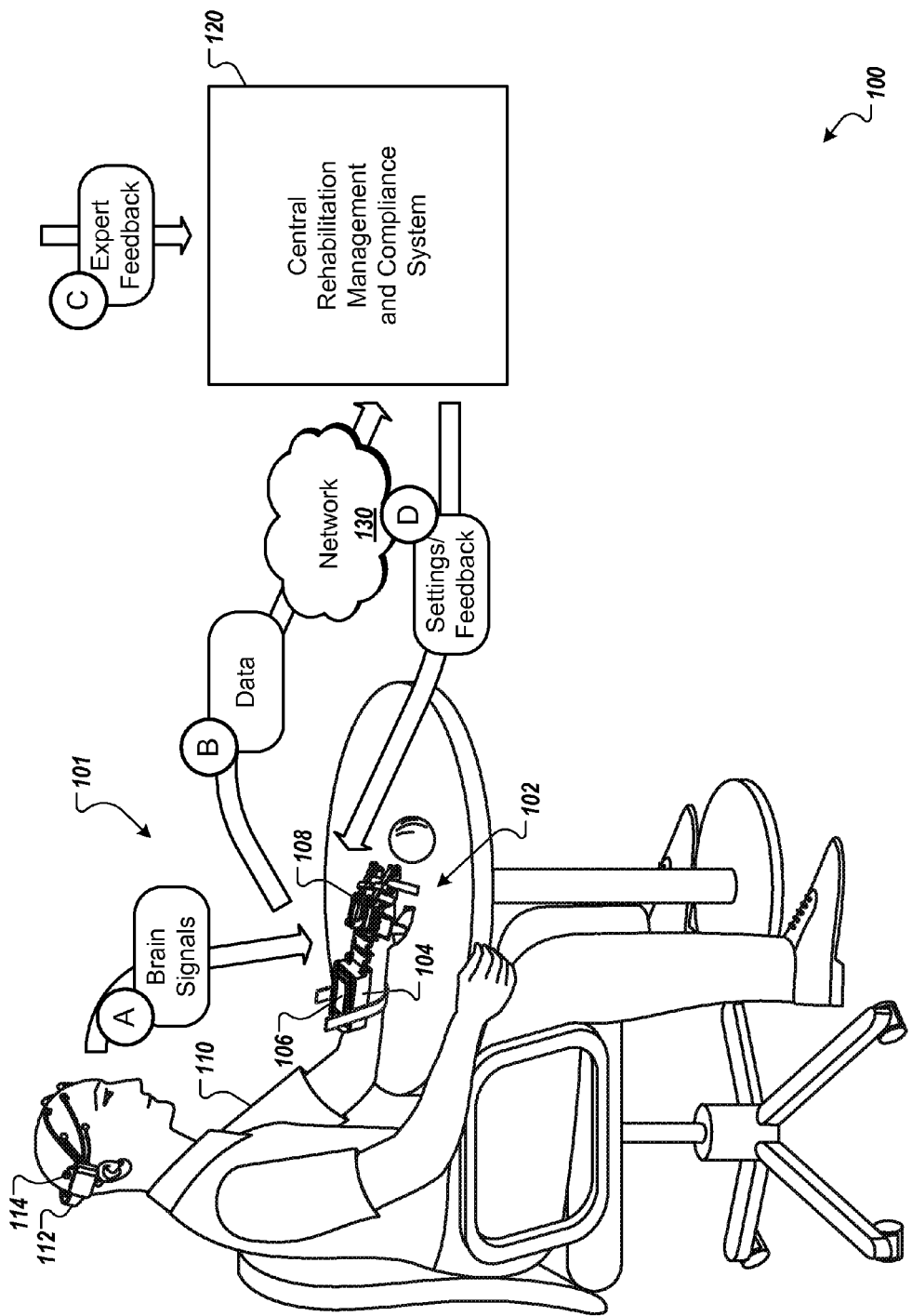
FIG. 1A is a diagram of an example BCI body movement assist system for brain injury rehabilitation, shown in use by a patient.

One example implementation, shown in FIG. 1A, is a brain-computer interface (BCI) body movement assistance system 100 which is adapted for use by a patient 110 who has experience brain injury (e.g., stroke, trauma, infection, hemorrhage, neonatal malformation, cerebral palsy, nedegenerative) to rehabilitate the patent's hand having impaired motor control. Generally, the system 100 includes: (i) a body-worn, and thus portable, BCI rehabilitation system 101, and (ii) a central rehabilitation management and compliance system 120. The body-worn rehabilitation system 101 includes: (i) a brain signal acquisition system 112, which in this example is a headset having several surface electrodes that acquire electroencephalogram (EEG) brain signals from multiple different and distributed surface locations on the patient's skin adjacent the brain, and (ii) a body-worn BCI and body movement assist device (BCI/assist device) 102, which in this example is adapted to be worn on the patient's hand and forearm and operates to assist the patient in moving the patient's four fingers. The central system 120 may be used in the set-up and on-going operation and monitoring of the body-worn rehabilitation system 101, and may be located remote from where the patient performs the rehabilitation activities using the wearable system 101, for example, at a healthcare facility or the facilities of some other type of rehabilitation services provider.

The brain signal acquisition system 112, shown in the FIG. 1A example, is a commercially available brain signal acquisition headset marketed and sold by Emotiv Systems. The acquisition system 112 acquires brain signals, performs low-level signal processing, and wirelessly transmits the EEG brain signals for receipt by the BCI/assist device 102. The EEG brain signals are acquired by the acquisition system 112 using a number of arranged surface electrodes 114 that are part of the acquisition system 112. Each of the surface electrodes 114 is located at an end of a corresponding arm that extends from a housing of the acquisition system 112 to a distal position such that, when the acquisition system 112 is worn by the patient, the electrodes 114 may be positioned to rest upon the patient's skin adjacent the brain. The electrodes 114 may be moistened, through application of a liquid or gel to the electrodes 114, before being applied to the patient's skin, which can increase conductivity with the patient's skin and can allow for brain signals to be detected and recorded with greater accuracy.

The brain signal acquisition system 112, although shown only from one side of the patient in FIG. 1A, may include electrodes 114 that may be positioned on both sides of the patient's head to acquire brain signals from both sides of the brain. That said, in a case of a patient having suffered a unilateral stroke, it may be that useful brain activity is only generated by one side of the patient's brain (namely, the side of the brain unaffected by the stroke). As such, it may be sufficient or only possible to acquire brain signals from one hemisphere of the patient's brain, in which case the brain signal acquisition system 112 may be designed accordingly for only one side of the patient's brain.

Although an EEG-based brain signal acquisition system 112 with skin surface electrodes is shown in the FIG. 1A example, other brain signal acquisition systems may alternatively be used. For example, acquisition systems with implantable electrodes may be used. For example, electrocorticography (ECOG) electrodes may be used and implanted under the skull of the patient and positioned so that the electrodes rest upon the brain surface but without penetrating into the brain tissue. Another example electrode system that may alternatively be used is a "point-style" electrode system that is also implanted beneath the skull of the patient, although this type of electrode system has electrode tips that penetrate into the brain tissue. Typically, such "point-style" implanted electrode systems include many prongs designed so that each of the prongs penetrates into the brain tissue at a different location.

Implantable electrodes may be desirable over surface EEG electrodes in that the acquired brain signals may contain greater information content regarding the intentions of the patient. For example, with implantable electrodes, it may be possible to discriminate intentions regarding the movement of each and every one of the patient's fingers, whereas that may not be possible, or at least may be more difficult, using brain signals acquired using surface EEG electrodes. That is because the skull may operate to block part of the brain signals, particularly at higher frequencies. That said, it will be recognized that implantable electrodes have the potential drawback of requiring a medical procedure to implant the electrodes.

The wearable BCI/assist device 102 is generally adapted to receive wirelessly transmitted signals containing information about the brain signals acquired by the acquisition system 112, process those received signals to determine patient intentions, and in accordance with determined patient intentions cause or assist the movement of the patient's fingers. Although in this example the wearable BCI/assist device 102 is designed and adapted to assist in the movement of the patient's fingers, in alternative implementations of this device 102 designed to improve motor activity in the hand and arm, the wearable BCI/assist device 102 may be designed so that it, additionally or alternatively, assists in the movement of the patient's wrist, thumb, elbow and/or shoulder. In alternate implementations, the wearable BCI/assist device 102 be designed and adapted to facilitate the movement of other extremities, such as the foot, ankle, knee or hip.

As shown, the wearable BCI/assist device 102 of the FIG. 1A example includes, (i) a BCI component 104, and (ii) a body movement assistance component 108 operably connected to the BCI component. The BCI component 104 generally includes the BCI processing capability and is adapted to be worn on an upper surface of the patient's forearm. The BCI component 104 may be attached to the forearm with, for example, a strap. The body movement assistance component 108 is generally connected by way of a hinge to the BCI component 104, and is adapted to be worn generally by the patient's hand (and in that sense, may be referred to as a glove). In particular, the movement assistance component 108 includes attachment mechanisms adapted to be attached to the patient's fingers, thumb and hand, and also has multiple controllable actuators that move in a manner that imparts movement onto the patient's fingers. In the FIG. 1A example, there are two body movement actuators. One movement actuator is attached to an attachment mechanism for both the index finger and the middle finger (a first finger pair), and imparts flexion and extension movement via the attachment mechanism onto those fingers. The other movement actuator is attached to a different attachment mechanism for both the ring finger and the pinky finger (a second finger pair), and imparts flexion and extension movement via that attachment mechanism onto those two fingers. As mentioned above, in some implementations the wearable BCI/assist device 102 may be designed and adapted to assist in the movement of the patient's wrist and/or thumb and/or individual fingers.

Figure 1B:
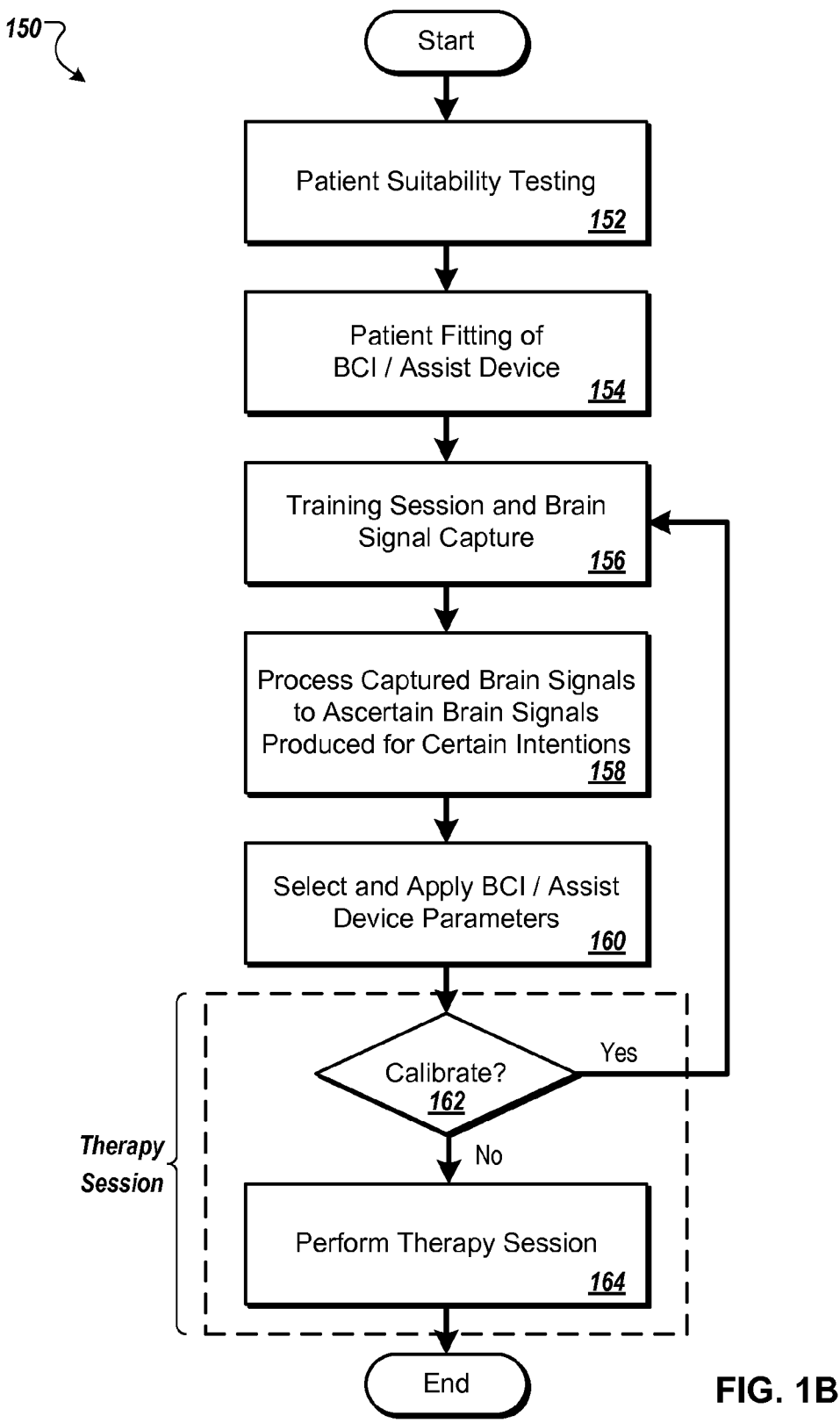
FIG. 1B is a flowchart of an example overall method of conducting rehabilitation therapy using a system such as that shown in FIG. 1A.

Referring to FIG. 1B, we turn now to a general process 150 of how the BCI system 100 shown in FIG. 1A may be used. For purposes of illustration and by way of example only, the following introductory description of use relates to a unilateral stroke patient undergoing rehabilitation of a motor impaired or paralyzed hand. That said, the devices and methods described in this specification are not limited to that stroke rehabilitation application.

The first thing that may occur for a stroke patient with impaired hand motor control is that the patient may undergo testing (step 152) to determine whether or not the patient is a suitable candidate for rehabilitation using the wearable BCI rehabilitation system 101. The timing along a rehabilitation/recovery timeline of when such a stroke patient may undergo the testing can vary. For instance, a stroke patient may undergo the testing (step 152) after acute or sub-acute rehabilitation, or after outpatient rehabilitation. One purpose of this suitability testing is to determine whether or not finger movement intentions can be ascertained from brain signals generated by the patient and acquired by the acquisition system 112. As an example, this suitability testing may be performed using the brain signal acquisition system 112 (appropriately selected and sized for the patient, and positioned on the patient's head appropriately) and the central system 120 (which may be capable of receiving the wireless transmissions directly from the brain signal acquisition system 112). In other words, suitability testing may be done without the need for the BCI/assist device 102, which may be appropriate given that the patient has not yet been deemed suitable for therapy using such a device 102. The suitability testing may be done, for example, at a rehabilitation clinic where the central system 120 is located, and under the supervision of a qualified BCI expert. Alternatively, suitability testing may be conducted with the patient located remote from the central system 120, with the remotely captured brain signals being transferred via network to the central system 120 for processing and analysis.

In some implementations, before performing the suitability testing described in the previous paragraph using the brain signal acquisition system 112 and the BCI/assist device 102 a patient may participate in a first round of suitability testing using a research grade EEG headset and BCI device (e.g., BCI2000) as part of the patient suitability testing (step 152). Such research grade equipment may be used to determine whether a patient is exhibiting any ipsilateral or motor derived signals for BCI use. The research grade equipment may be more sensitive to brain signals than the signal acquisitions system 112 and/or the BCI/assist device 102, and thus may be used as part of an initial screening process before screening is performed by the signal acquisition system 112 and the BCI/assist device 102. The screening using research grade equipment can involve similar procedures as those described with regard to the signal acquisition system 112 and the BCI/assist device 102. Alternatively, research grade equipment may also use anatomic or functional magnetic resonance imaging or magnetoencephalography to further augment suitability of a patient for a BCI system.

If a patient passes one or more screening tests using the research grade equipment, which may not be portable and which may be located in a clinic/research facility, the patient may proceed to screening using the signal acquisition system 112 and the BCI/assist device 102. The screening process using the signal acquisition system 112 and the BCI/assist device 102 can involve displaying real-time (near real-time) results on a display of the BCI/assist device 102, comparing the results with those from the research grade screening for consistency with regard to detected ipsihand control features for the patient (e.g., brain signal that has been determined to indicate and correspond to user intent to move a body part along the same side of the user's body as the side of the brain where the signal was detected—an ipsilateral brain signal), and using the detected ipsihand control features to perform cued control (e.g., device directed actions by the patient) to accomplish one or more tasks (e.g., moving a graphical bar displayed by the BCI/assist device 102 past a threshold level). If the patient successfully performs one or more of the tasks, the patient may be identified as a candidate for the rehabilitation using the signal acquisition system 112 and the BCI/assist device 102. Additionally, the signal acquisition system 112 may detect specific physiologic features (e.g., a specific frequency band, amplitude modulation, or phase or time series related phenomenon) that may predict the patient's response to a rehabilitation regime.

Assuming the patient is a suitable candidate for the rehabilitation, the patient may then be fitted (step 154) with an appropriately sized wearable BCI/assist device 102. It may be that the rehabilitation clinic will have several sizes on hand for the wearable BCI/assist device 102. Alternatively, the BCI/assist device 102 may be manufactured on site and sized specifically for the patient, for example, using three-dimensional (3D) printing or other on-site customized manufacturing techniques. For example, three-dimensional scans of a patient can be performed, and a customized model of the BCI/assist device 102 can be manufactured for the patient, based on the scanned measurements.

Next, the patient may undergo initial training exercises (step 156), which may be done, for example, also at the rehabilitation facility, and under the supervision of a qualified BCI expert. The purpose of initial training exercises is to ascertain what specific brain signals that the acquisition system senses when the patient is planning and executing certain intended movements (the sensed brain signals may include, for example, the electrode or electrodes at which changes from a baseline signal level are detected, thus indicating some brain activity, and at what magnitude and signal frequency that brain activity was sensed.

To do these initial training exercises, the patient may be prompted to try to accomplish various finger movements, and when the patient is preparing to perform, and in the process of attempting to perform, those tasks, the brain signals produced during that time may be acquired and eventually stored in memory of the wearable BCI/assist device 102. The finger movement prompts may be provided by the wearable BCI/assist device 102, for example, using visual displays provided on the BCI component's display device 106 and/or using other sensory prompts (e.g., audio signal prompts, vibrotactile prompts, etc.) produced by the BCI/assist device 102. As those prompts are being provided to the patient, the brain signal acquisition system 112 continuously captures brain signal samples sensed at each of the multiple electrodes (magnitude at various frequency levels).

The initial training exercises may include several distinct calibration exercises during which specific brain signals are tested and various levels of feedback are provided to the patient. For instance, in a first calibration exercise a patient can be cued/prompted to alternate between resting and generating ipsilateral brain signals (e.g., think of moving right hand). This first calibration exercise can be configured to assess whether the patient is able to generate sufficient physiological change with regard to the previously identified control feature(s). The ipsilateral movement performed by the user can be compared against periods of rest to make such an assessment. During this first calibration exercise, feedback may not be provided to the patient. In a second calibration exercise, a patient may be prompted/cued to generate ipsilateral signals (e.g., think of moving right hand) to control an object that is presented on a display 106 of the BCI/assist device 102, such a bar that moves based on the strength of ipsilateral signals that are generated by the patient. In a third calibration exercise, a patient may be prompted/cued to generate ipsilateral signals that will control movement (e.g., opening and closing) of the body movement assist component 108 of the BCI/assist device 102. The cues can be presented on the display 106 of the BCI/assist device 102 and feedback can be provided in the form of movement of the BCI/assist device 102, as well as through sensory feedback (e.g., playing sound, engaging a vibrotactile device, delivering electrical stimulation) and/or other visual feedback (e.g., presenting information on the display 106). The sampling rate of the brain acquisition system 112 may be, for example, 256 Hz and/or 512 Hz.

Signals containing representations of the captured brain signals and other relevant information are then transmitted wirelessly by the acquisition system 112 for receipt by the BCI/assist device 102, as illustrated in FIG. 1A by Arrow A. The signal representations that are received by the acquisitions system 112 can be in any of a variety of appropriate forms, such as amplitude, power modulation, phase alteration, change in event related potential, and/or change in the raw time series of the signal.

The brain signal information received by the wearable BCI/assist device 102 from the acquisition system 112 will typically be time-stamped in some manner and stored in memory of the BCI/assist device 102. This allows, for example, the timing of the acquired brain signals vis-à-vis the timing of the prompts to the patient to be correlated. After a series of training prompts are completed (and brain signal and timing information is stored in memory of the BCI/assist device 102), the acquired data may be transferred from the BCI/assist device 102 to the central system 120 for evaluation and processing, as illustrated by Arrow B in FIG. 1A.

Generally, the central system 120 performs computer processing (step 158) on the data to ascertain what brain signals (electrodes, magnitudes and frequencies) the patient produced when the patient was planning and attempting to execute the various finger movements that the patient was prompted to perform. The central system 120 may then determine (step 160), from the ascertained brain signals, appropriate parameter settings and/or control features for the BCI/assist device 102, which can include electrodes specification, frequency band, and/or changes in power or amplitude of the signal. The central computer 120 may perform this analysis and feature selection, at least in part, using input from a technician.

The central system 120 then will transfer those parameter settings to the wearable BCI/assist device 102, as indicated by Arrow D in FIG. 1A, so that the parameter settings are used during the patient's rehabilitation exercises. In some implementations, the information transmitted to the BCI/assist device 102 may include instructions such as a series of suggested rehabilitation sessions (e.g., an optimal type and manner) for the patient, and other configurable settings such as time limits between calibration sessions.

The patient is now able to perform rehabilitation exercises using only the portable, wearable BCI rehabilitation system 101 (that is, only the brain signal acquisition system 112 and the wearable BCI/assist device 102). Owing to the portable nature of the BCI rehabilitation system 101, the patient may perform the rehabilitation exercises outside of a rehabilitation clinic. For example, the patient may perform the exercise in the patient's home. Such home delivered rehabilitation is believed to assist in the rehabilitation efficacy of the system. For example, the portability and wearable aspects of the BCI rehabilitation system 101 can increase the number of opportunities to use the system 101, which can increase the number of repetitions that a patient performs using the system 101. Such an increase in the number of repetitions is believed to be positively correlated to improved functional outcomes for patients. Additionally, the portability and wearable aspects of the BCI rehabilitation system 101 permit for the system 101 to be used in and integrated into a patient's daily life, which can allow for a patient to perform rehabilitation tasks that are context dependent (e.g., folding laundry, opening doors, picking-up and organizing belongings) rather than rote (e.g., repeatedly opening and closing hand without specific purpose). Such context-dependent rehabilitation tasks are also believed to positively impact functional outcomes for patients. Taken in combination, the ability to perform physical tasks using the system 101 more frequently and within the context of a patient's daily life is likely to enhance the brain plasticity and rehabilitation benefits beyond classic in-patient settings with predefined periods of therapy.

To set up the rehabilitation session, the patient will first put on the brain signal acquisition system 112 (e.g., headset), and position and secure the electrodes 114 in place against the skin adjacent the brain. Ideally, the electrode positions will be positioned in rehabilitation as they were in the training exercise, but in reality, that is not always possible; that is why a calibration process (step 162) may be utilized, as will be discussed in more detail below. The patient will then put the wearable BCI/assist device 102 on the patient's forearm and hand as described previously, namely, by securing the BCI component 104 to the forearm and the finger-pair and thumb attachments of the movement assistance component 108 accordingly. The patient may then activate (turn on) both the headset 112 and the BCI/assist device 102 to start the rehabilitation session.

The rehabilitation session (step 164) may be performed in a variety of ways. In one scenario, the patient performs any finger movement desired of the types addressed in the training session. For example, the patient may first desire to perform ten repetitions of flexing and extending the index/middle finger pair. In this example, the patient first attempts a finger pair flexing movement, and in doing so produces certain brain signals corresponding to the planning and execution of that finger pair movement. The brain signal acquisition system 112, during the entire rehabilitation session, acquires periodic samples of brain signals and wirelessly transmits those samples to the BCI component 104 for evaluation (at, e.g., 256 or 512 samples per second). Each sample may include a set of information including parameters (e.g., magnitude, frequency) of the signal sensed at each of the multiple electrodes. The BCI component 104 processes those brain signal samples to determine the patient's intentions. If and when the BCI component 104 detects that the patient has produced brain signals indicating that the patient intends to flex the index and middle finger pair, the BCI component will produce a control signal that activates the movement assistance device 108 to assist in the patient's movement of the index and middle finger pair.

During the rehabilitation session (step 164), the patient may be given continuous feedback via the BCI/assist device 102. Feedback may take several forms, and improves in the overall efficacy of the rehabilitation session. In general, feedback provided to a patient may be in the form of visual, acoustic, tactile (e.g., vibrotactile) and/or electrical stimuli that supplement a control response. One example of feedback is that the BCI/assist device 102 may provide an indication to the patient that a particular intention has been detected. One example way that this may be done is for the BCI/assist device 102 to produce a visual display (on display device 106) showing, for example, that the BCI component 104 has detected a particular intention, for example, that a flexion movement of the index/middle finger pair be performed. Given the positioning of the display device 106 on the top of the patient's forearm, the patient will easily be able to see that this particular intention was detected by the system 101. Another example way that feedback may be presented is for the BCI/assist device 102 to generate sound using the BCI component 104 (e.g., using a speaker included in the component). For example, the BCI component 104 may produce tones, or may produce recorded spoken feedback, such as "opening hand". Another example way that feedback may be presented is for the BCI/assist device 102 to produce tactile feedback and/or electrical stimuli using the body movement assistance component 108. For example, upon identifying a user's intention to open his/her hand, the BCI/assist device 102 may use the body movement assistance component 108 to provide tactile (e.g., vibrotactile) feedback to the user and/or to provide electrical current to the user's hand. In some implementations, multiple forms of feedback may be provided to a user simultaneously. Simultaneous presentation of visual, acoustic, tactile, and/or electrical feedback may simultaneously excite multiple areas of a patient's brain, for example, and may encourage neuroplasticity.

The rehabilitation session (step 164) can include prompts/cues that instruct the patient to perform particular actions using the system 101. In general, prompts/cues may include one or more visual, acoustic, and/or tactile elements. For example, the display device 106 can display cues for the patient to move his/her right hand (e.g., open right hand, close right hand), to move his/her left hand, and/or to rest. The BCI component 104 can generate the prompts to be displayed on the display 106 (and/or output to the user through one or more other output mechanisms, such as a speaker and/or tactile device that is part of the BCI component 104) based on a variety of factors, such as a predetermined therapy schedule generated by the central rehabilitation management and compliance system 120, current progress by the user (e.g., number of repetitions performed, progress along a therapy schedule), and/or information obtained by sensors of the BCI/assist device 102 (e.g., levels of force detected by pressure sensors in the BCI/assist device 102 indicating degrees to which a patient is driving movement of the BCI/assist device 102 and/or emergence or regression of brain signals or features detected by the brain signal acquisition system 112).

The BCI/assist device 102 can also operate in a free assist mode (step 166) during which a patient is able to use the BCI/assist device 102 to perform tasks within the context of the patient's daily life. During a free assist mode, the BCI/assist device 102 can interpret brain signals detected by the brain signal acquisition system 112 to determine what actions, if any, the user intended for the BCI/assist device 102 to perform, such as opening and/or closing a hand onto which the BCI/assist device 102 is mounted. The BCI/assist device 102 can provide a user interface, such as on the display 106, which can provide feedback to the patient regarding the type of action that the BCI component 104 has determined that the user intended through brain signals detected by the brain signal acquisition system 112. The BCI/assist device 102 can perform actions (e.g., closing fingers, opening fingers) that the BCI/assist device 102 determined to have been intended by the patient so as to enable the patient to interact with his/her environment more fully using the body part (e.g., hand) on which the BCI/assist device 102 is mounted. For example, during the free assist mode (step 166) a patient can generate brain signals to cause the BCI/assist device 102 to close and open the patient's left hand when needed in order to open and close doors, to pick up objects around the patient's house, to fold laundry, and other daily tasks. As explained above, such contextual use of the BCI/assist device 102 in the patient's daily life can enhance the rehabilitation for the patient.

With this type of feedback, if for example the patient is intending a particular movement and the portable BCI rehabilitation system 101 is not responding by assisting the patient in performing that movement, the patient will know immediately that the problem lies with the system 101 not detecting the patient's intention, and not some other problem. One cause of the intention not being detected may be that the electrodes 114 of the headset 112 may not be in their proper positions, and adjustments to the positioning may solve the problem. Another cause of the intention not being detected may be that the patient's brain signals may have evolved over time during the rehabilitation process, via a process known as brain plasticity wherein neural pathways become reorganized. This in many cases may be a positive development for the patient, in that additional or different brain activity is occurring to compensate for the brain areas that were damaged by the stroke. For example, specific features may correlate with these plastic changes, such as an alteration in amplitude of a specific frequency band or a change in phase interaction between two cortical sites. As such, it may be appropriate for a calibration process (step 162) to be performed to update the system 101 regarding the brain signals that the patient produces for a particular finger movement intention.

To perform this calibration process (step 162), the patient may perform a new training process similar to the one performed during set-up, or an abbreviated version of that training process. This calibration process may be guided by the BCI/assist device 102, for example, using appropriate displays on the display device 106. For example, the BCI/assist device 102 may guide the patient through a number of finger exercises, and during that time obtain and store brain signal information in memory of the BCI/assist device 102. At the end of the calibration process, the patient may initiate a process wherein the data obtained during the calibration process is transmitted from the BCI/assist device 102, over a network 130, to the central system 102, as indicated by Arrow B in FIG. 1A. The central system 102 may evaluate that data as described previously in connection with the initial training process, and once that is complete, transmit updates including updated operational parameters to the BCI/assist device 102 for use in the next rehabilitation session. As such, this calibration process may be performed remotely of any rehabilitation clinic where the central system 120 is located.

Another example of feedback that the BCI/assist device 102 may provide to the patient relates to the status of a particular rehabilitation session, and even more generally, to the status of attaining certain goals of the overall rehabilitation effort. In general, information may be provided in association with measured phenomenon from the BCI/assist device 102 and the brain signal acquisition system 112. Feedback provided to the patient, for example, can include information associated with repetitions during one or more rehabilitation sessions, and time of day and duration of use, which may be derived from the BCI/assist device 102. Further, information associated with changes that may occur in the patient's brain physiology can be measured, documented, and presented (e.g., in the form of a graphic representation showing increased or decreased presence of signals associated with the performance of a task or in signals not associated with the task but associated with a rehabilitation outcome). For example, for a specific rehabilitation session, the BCI/assist device 102 may record the number of repetitions that the patient has done of a particular finger movement, and display that for the patient on the display device 106. The BCI/assist device 102 may also display suggested exercises to the patient. In addition, the BCI/assist device 102 may also display a measure of force that had to be applied to the fingers to aid in the intended movement. If, for example, less and less force is being required to assist in the intended movement, this may indicate to the patient that progress is being achieved by the rehabilitation effort. The BCI/assist device 102 may also display, for example at the end of a rehabilitation session, a summary report of all of the exercises that were performed during the rehabilitation session, and in addition a general assessment of the patient's progress toward certain goals with the rehabilitation effort.

The system 100 shown in FIG. 1A also enables remote monitoring of the patient's rehabilitation efforts and progress. For example, the portable rehabilitation system 101 may periodically send reports via network 130 to the central rehabilitation and compliance system 120. The reports may indicate, for example, compliance information, namely, whether or not the patient has carried out required or suggested rehabilitation sessions. In addition, the reports provided to the central system 120 may be reviewed by a health care provider or other rehabilitation specialist to see what if any progress is being made with the rehabilitation effort, and provide instructions for future therapy sessions, feedback, and perhaps encouragement to the patient where appropriate, as indicated by Arrow C in FIG. 1A. In some implementations, information included in reports from multiple patients may be anonymized and aggregated to identify factors and trends which may generally lead to improved rehabilitation results for patients. By analyzing overall device usage statistics (e.g., time of use, number of repetitions, etc.) and patient characteristics (e.g., type of impairment, age, etc.), for example, the central rehabilitation management and compliance system 120 may identify groups of patients who may generally benefit from particular types of therapy. For example, the system 120 may determine that a patient (e.g., a stroke patient of a certain age) may benefit from a particular type of therapy session (e.g., a session including a certain number of repetitions at a certain time of the day), based on the progress of similar patients (e.g., other stroke patients of a similar age) having conducted similar therapy sessions. Health care provider feedback and therapy session instructions may be provided to the patient, for example, on the display device 106 of the BCI/assist device 102 at the beginning of the patient's next rehabilitation session.

Figure 2:
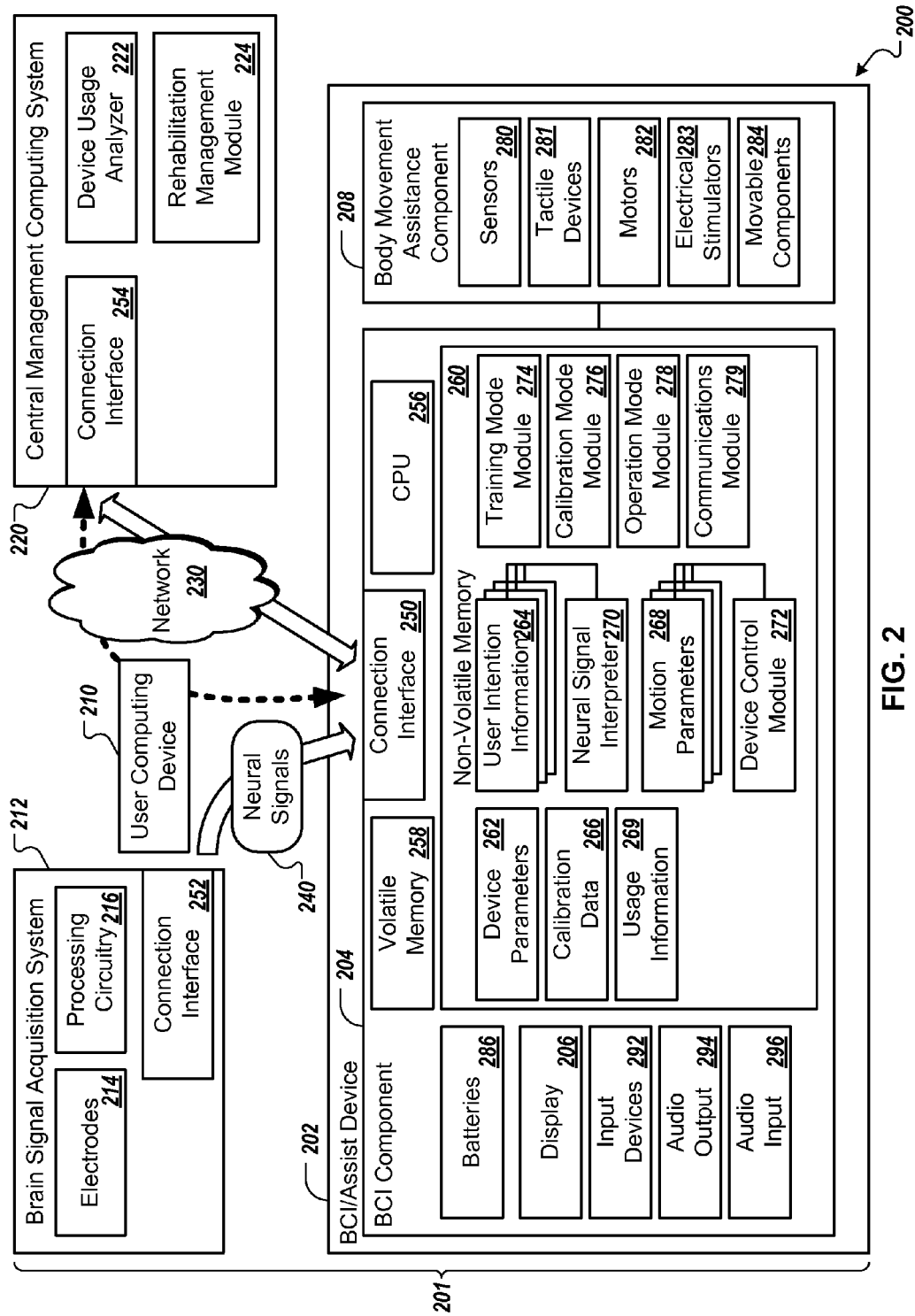
FIG. 2 is a block diagram of an example BCI body movement assist system.

Referring now to FIG. 2, there is shown a generalized block diagram of a brain-controlled body movement assist system 200. This block diagram of FIG. 2 describes not only the example system 100 shown in FIG. 1A, but also other embodiments of brain-controlled body movement assistance systems, for example, systems for the control of other body movements (e.g., arm, shoulder, elbow, wrist, hand, leg, knee, ankle, foot, etc.), and systems that use different types of brain signal acquisition systems other than the EEG brain signals as shown in the FIG. 1A implementation (e.g., implantable electrodes).

As shown in FIG. 2, the brain-controlled body movement assist system 200 includes: (i) a body-worn, and thus portable, BCI movement assistance system 201, and (ii) a central management computing system 220. The body-worn BCI movement assistance system 201 includes two main components: (i) a brain signal acquisition system 212, and (ii) a body-worn BCI and body movement assist device (BCI/assist device) 202. The central management computing system 220 may be used in set-up and on-going operation of the body-worn BCI movement assistance system 201, and may be located at a location that is remote of the patient, for example, at a healthcare facility or the facilities of some other type of services provider.

Generally, the brain signal acquisition system 212 acquires brain signals, performs low-level signal processing, and transmits the brain signals for receipt by the BCI/assist device 202. The brain signals are acquired by the acquisition system 212 using a number of arranged electrodes 214 that are part of the acquisition system 212. As discussed previously, these electrodes may be EEG surface electrodes or implantable electrodes (for example, ECOG electrodes or "point-style" electrodes). The acquired neural signals, for example, may also include magneto encephalography (MEG) signals, mu rhythm signals, beta rhythm signals, low gamma rhythm signals, high gamma rhythm signals, action potential firing, and the like. The brain signal acquisition system 212 also includes processing circuitry 216 to perform the low-level processing and formatting of brain signal information for transmission to the BCI/assist device 202, and a connection interface 252 to enable that transmission. The connection for transmission between the brain signal acquisition 202 and the body-worn BCI assistance device 202 may be wireless or hard-wired, and thus the connection interface 252 would be adapted accordingly to enable the wireless or hard-wired transmissions. For example, the connection interface 252 may include USB drivers, Bluetooth drivers, or some other wireless or hard-wired transmission protocol interface mechanisms and circuitry.

As mentioned, the body-worn BCI and body movement assist device (BCI/assist device) 202 includes two main components, (i) a BCI component 204, and (ii) a body movement assistance component 208 operably connected to the BCI component 204. The BCI component 204 generally includes the BCI processing capability and is adapted to be worn on a user (e.g., on the user's forearm as in the FIG. 1A example or some other body part in other implementations). The body movement assistance component 208 is operably connected to the BCI component 204, and also is adapted to be worn by the user (e.g., on a user's hand as in the FIG. 1A example or some other body part to be moved in other implementations).

The BCI component 204 includes the processing and control circuitry to operate the BCI/assist device 202 in training modes, operational modes (e.g., rehabilitation sessions), calibration modes, and communications modes. As such, the BCI component 204 includes one or more processing units such as a central processor unit (CPU) component 256, volatile memory 258 such as random access memory (RAM), and non-volatile memory 260 such as read-only memory (ROM) and/or various forms of programmable read-only memory (PROM) for the storage of software or firmware programs and operating parameters that may be periodically updated. The BCI component 204 may also include one or more of the following additional hardware components: (i) one or more batteries 286 to enable the BCI/assist device 202 to be portable (the batteries 286 can provide power to the various components of the device 202, and may be recharged via an adapter or charging device (not shown here)), (ii) visual output display equipment 206 including visual displays and related display drivers and circuitry, (iii) user input devices 292 such as on/off and other buttons or touch-screen displays to enable manual user input, (iv) audio output equipment 294 to provide audio commands, information and prompts to the user, (v) audio input equipment 296 such as a microphone to receive audio input from the user, and (vi) connection interfaces 250 to enable communication between the BCI component 204 and the brain signal acquisition system 212 for example to receive wirelessly or hard-wired transmitted neural signals 240, and also between the BCI component 204 and the central system 220 via network 230.

As mentioned briefly above, the BCI assist device 202 can include various components for providing information to and receiving input from a user. The visual output display equipment 206, for example, may be a regular or touch screen display for providing visual prompts (e.g., graphics, instructions, etc.) or other sorts of information to the user and/or for receiving user input. The input devices 292, for example, may include one or more buttons for controlling (e.g., pausing, powering on/off, sending data, receiving data, changing modes, etc.) the BCI/assist device 202. For example, the input devices 292 (e.g., buttons) may serve as soft keys alongside the display equipment 206 and/or may be situated away from the display equipment 206. The audio output equipment 294 (e.g., speakers), for example, may be used for providing auditory prompts (e.g., live or recorded spoken instructions, tones indicating success or error conditions, etc.). The audio input equipment 296 (e.g., microphone), for example, may be used for receiving spoken input from the user (e.g., voice controls) and/or may serve with the audio output equipment 294 for conducting a live communication session with a remote technician.

In terms of software and/or firmware programs, the BCI component 204 may include various programs that are stored in non-volatile memory 260 that include executable program instructions that are executed by the CPU 256 to carry out the various processing functions. This may include one or more of the following program modules: (i) a neural signal interpreter 270 for interpreting neural signals received from the brain signal acquisition system 212, and specifically determine whether those received signals are indicative of a user intention to perform certain predefined body movements which will be assisted by the body movement assistance component 208; (ii) a device control module 272 for providing control signals to the body movement assistance component 208 to actuate movement; (iii) a training mode module 274 for carrying out the training processes; (iv) an operational mode module 278 for carrying out the operation of the BCI/assist device 202 in normal operation, for example, in a rehabilitation session, (v) a calibration mode module 276 for carrying out the operations calibration processes, and (vi) a communications module 279 for carrying out communications processes between the BCI/assist device 202 and the central management system 220.

The non-volatile memory 260 may also include information storage areas for operational parameter settings or other input information used during the operation of the BCI component 204. The settings and other input information may be input by a user, or may be transmitted to the BCI component 204 from the central system 220. These information storage areas may include one or more of the following: (i) device parameter setting storage 262 for storing various operational parameter settings that may be, for example, selected by a user or selected and provided by the central management system 220, (ii) user intention information storage 264 for storing one or more sets of previously ascertained brain signals, each set being indicative of a user intention to perform a different body movement, and specifically movements that are assisted by the movement assistance component 208 (this intention information being for use by the neural signal interpreter program 270), (iii) calibration data storage 266 for collected calibration data including brain signal information that is collected during a calibration session, and which may be retrieved and sent by the BCI component 204 to the central system 220 for evaluation, (iv) body motion range parameter settings 268 (which may be used by the device control module 272) comprising parameter settings that dictate a range of motion by the assistance component 208 (for example, to what extent will a finger be flexed and extended), and (v) usage information storage 269 wherein information regarding the usage of the wearable BCI/assist device 202 by the user may be stored, for example, how many times the device has been used, for how long, when, and what the results of each usage session were (which usage information may be retrieved and sent by the BCI/assist device 202 to the central management system 220).

The movement assistance component 208 operates under the control of the BCI component 204, and can include various components to assist in body movement (e.g., an external robotic assist device, a prosthetic device, a functional electrical stimulation (FES) device, etc.). For example, the movement assistance component 208 in the FIG. 2 example includes one or more sensors 280, tactile devices 281, motors 282, electrical stimulators 283, and movable components 284 that may be fixed to the body part. The sensors 280, for example, may be used to detect the amount of force applied to the body part in order to assist in the movement of the body part and/or to detect the position of the moveable components 284. Such force detectors may provide information as to whether the patient is effectively moving the body part on the patient's own, and if not, how much assistance was needed in order to effectuate the body movement, and is the patient's motor control such that the patient is resisting the movement without intending that. The position detectors may be used, for example, to tell the BCI component 204 that the fingers are now fully flexed, fully extended, or at some intermediate position. Information collected by the sensors 280 can be provided to the device control module 272, the training mode module 274, the calibration mode module 276, and the operational mode module 278.

The tactile feedback devices 281, for example, can provide tactile feedback (e.g., vibrotactile feedback) to a user in association with a prompt and/or in association with an identified user intention. In some implementations, to prompt the user to move a body part (e.g., a hand), a tactile device may operate (e.g., vibrate), alone or in combination with other sorts of prompt mechanisms (e.g., visual and/or acoustic). Similarly, to indicate to the user that an intention to move a body part has been identified, in some implementations a tactile device may operate (e.g., vibrate), alone or in combination with other feedback mechanisms (e.g., visual and/or acoustic).

The motors 282, for example, may include rotary, servo, and/or linear motors for driving gears, pistons, and the like. The device control module 272 executed by the central processing unit 256, for example, can provide signals for controlling the motors 282. The movable components 284 can be coupled to and moved by the motors 282, for example, and can include one or more mechanisms for guiding or assisting the movement of a corresponding body part.

The electrical stimulators 283, for example, can use electrical currents to activate the muscles or nerves of a device user's affected body part. For example, upon identifying the user's intention to move a body part (e.g., a hand), the electrical stimulators 283 can deliver electrical current to the body part, thus facilitating movement. In some implementations, electrical stimulation of body parts may be provided alone or in combination with mechanical mechanisms for guiding or assisting the body parts.

The central management computing system 220, for example, can include one or more computing devices configured to receive information from the BCI/assist device 202 (and the BCI component 204 in particular), to execute one or more applications for processing, analyzing, and tracking the data, and to provide operation and configuration data to the BCI/assist device 202. For example, the central system 220 can execute computer application code associated with a device usage analyzer 222 and a rehabilitation management module 224. The device usage analyzer 222, for example, can be used by a technician for analyzing information received by the BCI/assist device 202 and for determining operation instructions and parameters to be used by the device. The rehabilitation management module 224, for example, can be used by the technician for tracking a device user's progress over time, and for configuring the BCI/assist device 202. In some implementations, the central system 220 may be similar to the central system 120 described above with respect to FIG. 1A.

The wearable BCI/assist device 202, the acquisition system 212, and the central system 220 can each include a connection interface (e.g., connection interfaces 250, 252, and 254, respectively) for receiving data from and providing data to other devices through wired and/or wireless connections. For example, the connection interfaces 250, 252, and 254 may include USB drivers, Bluetooth drivers, WiFi drivers, and/or mobile data connection drivers, such as 3G drivers, 4G LTE drivers, and 4G WiMAX drivers. The connection interface 250 of the BCI/assist device 202, for example, can be configured to receive neural signal data 240 from the connection interface 252 of the brain signal acquisition system 212. The connection interfaces 250 and 254, for example, can be configured to send and receive data between the BCI/assist device 202 and the central system 220 through the network 230. In some implementations, the network 230 may similar to the network 130 described above with respect to FIG. 1A.

The system 200 may additionally include a user computing device 210, such as a laptop computer, a desktop computer, a smartphone, a tablet computing device, a personal digital assistant (PDA), and/or a media computing device. The user computing device 210 may be located at or near a location where the BCI/assist device 202 is stored and used, such as at a user's home. The user computing device 210 may communicate with the BCI/assist device 202, such as through a local area network, and may obtain rehabilitation data (e.g., log of rehabilitation sessions, summary of repetitions performed, duration of use, and progress along a rehabilitation schedule) from the use of the BCI/assist device 202. The user computing device 210 can present the rehabilitation data through a user interface that may be easier to use and interact with than a user interface provided through the display 206 of the BCI/assist device 202. Additionally, the user computing device 210 can communicate with the central management computing system 202 through the network 230 to view rehabilitation data. For example, the user computing device 210 can include one or more applications (e.g., web browser) that may authenticate the user associated with the user computing device 210 (e.g., login) and that may provide access to rehabilitation data that has been provided by the BCI/assist device 202 to the central management computer system 220.

Figure 3:
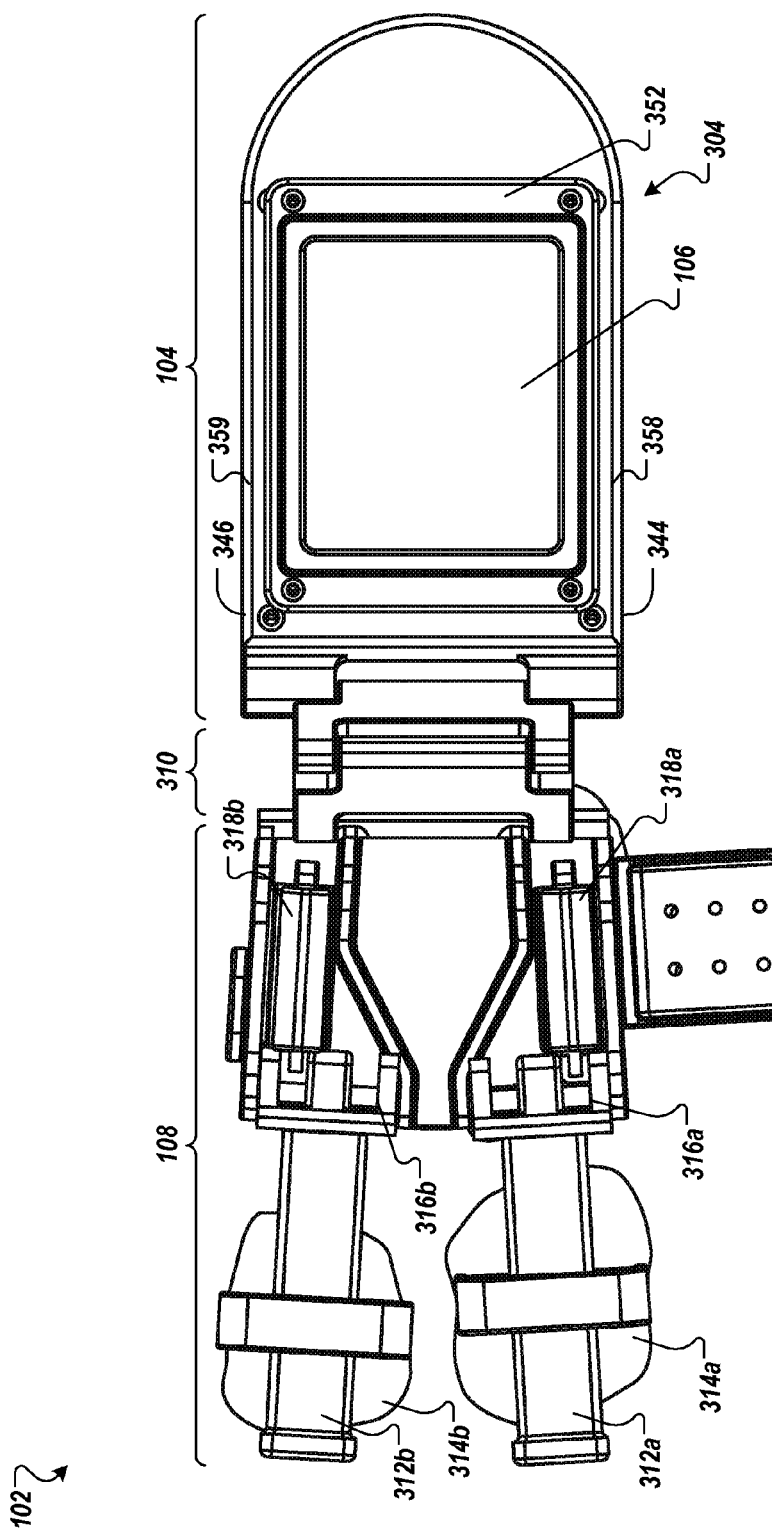
FIGS. 3-6 are diagrams of the wearable BCI/assist device shown in FIG. 1A, from, respectively, top, thumb-side, bottom and distal-end (front) views.
Figure 4:
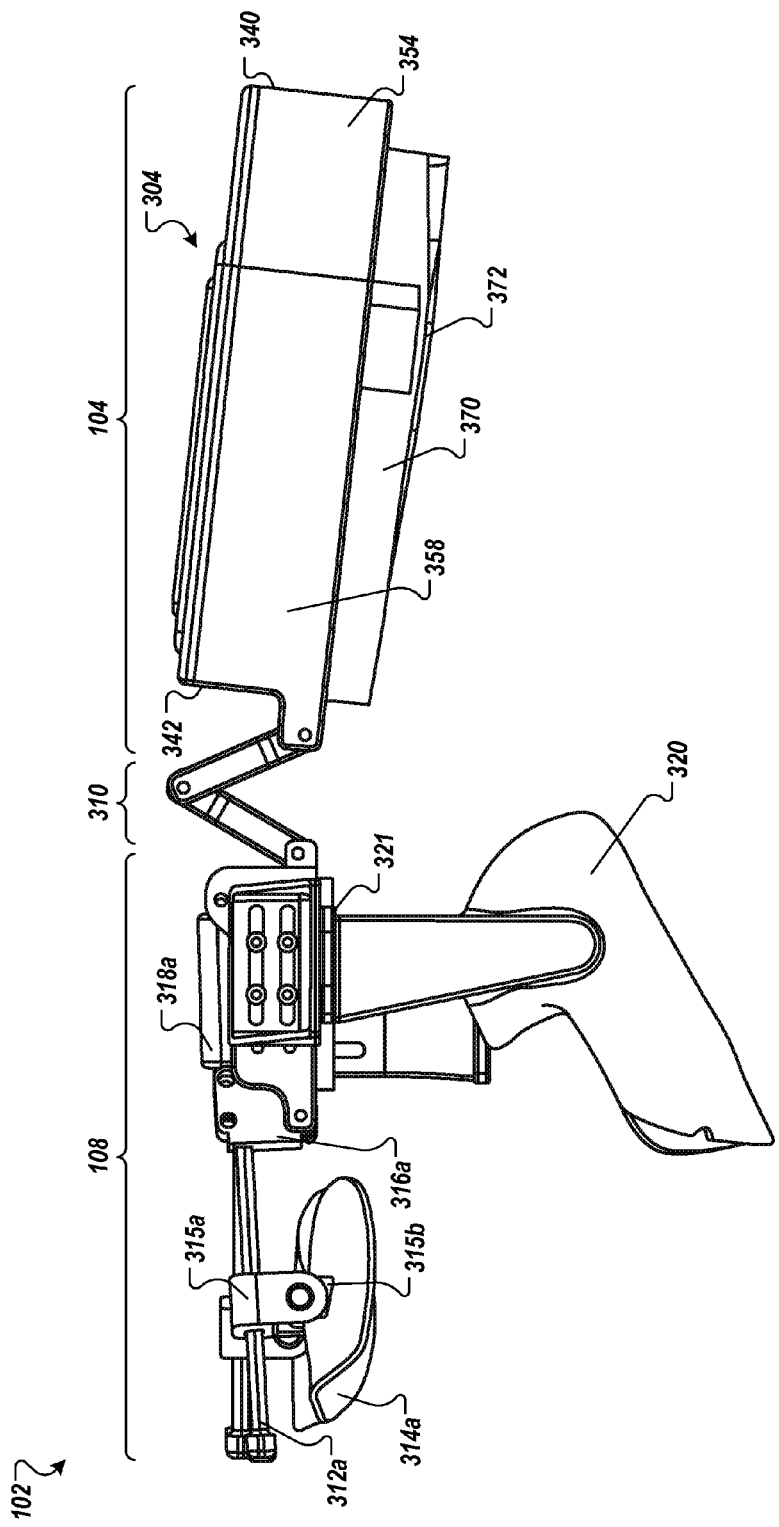
Figure 5:
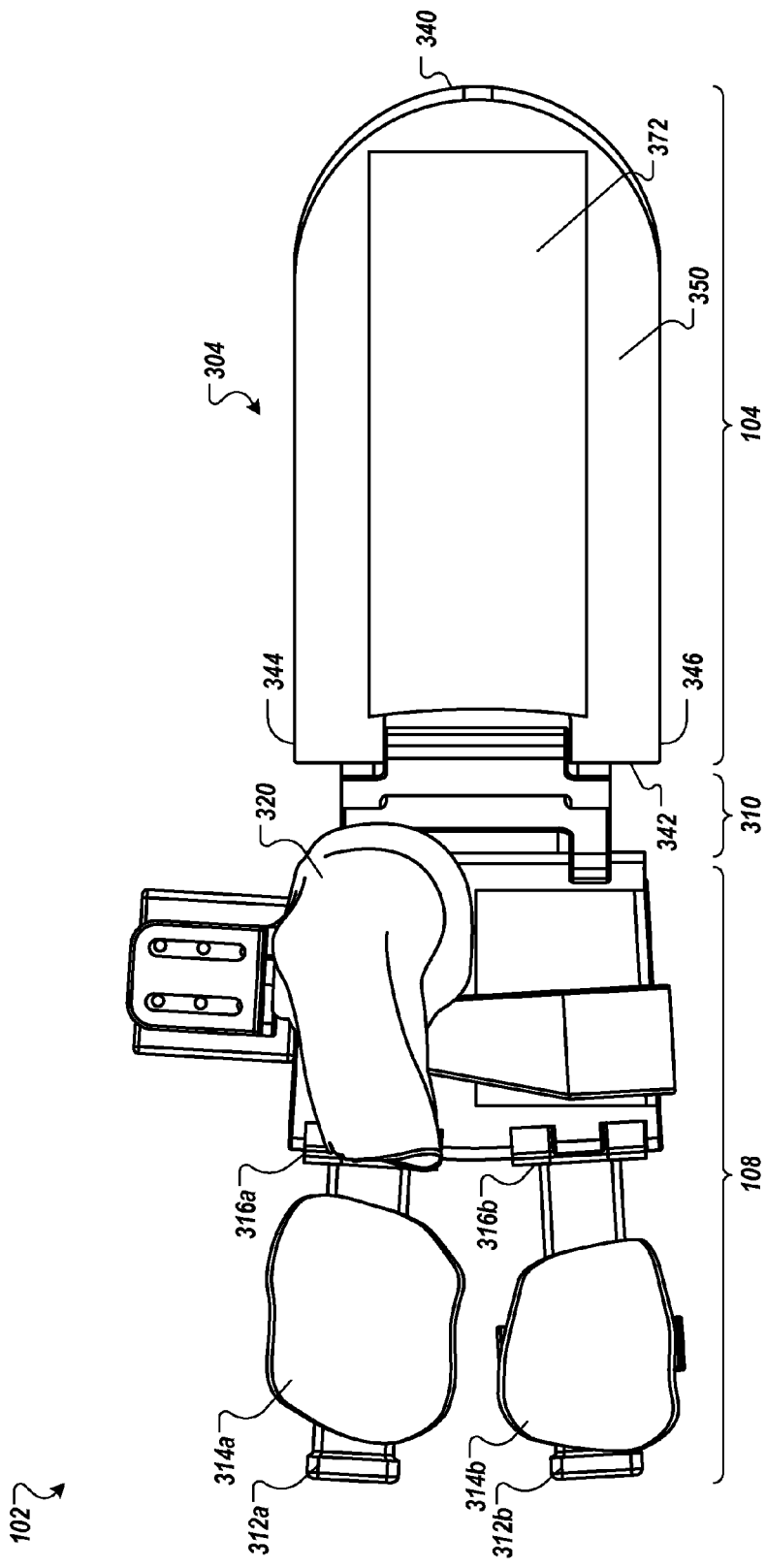
Figure 6:
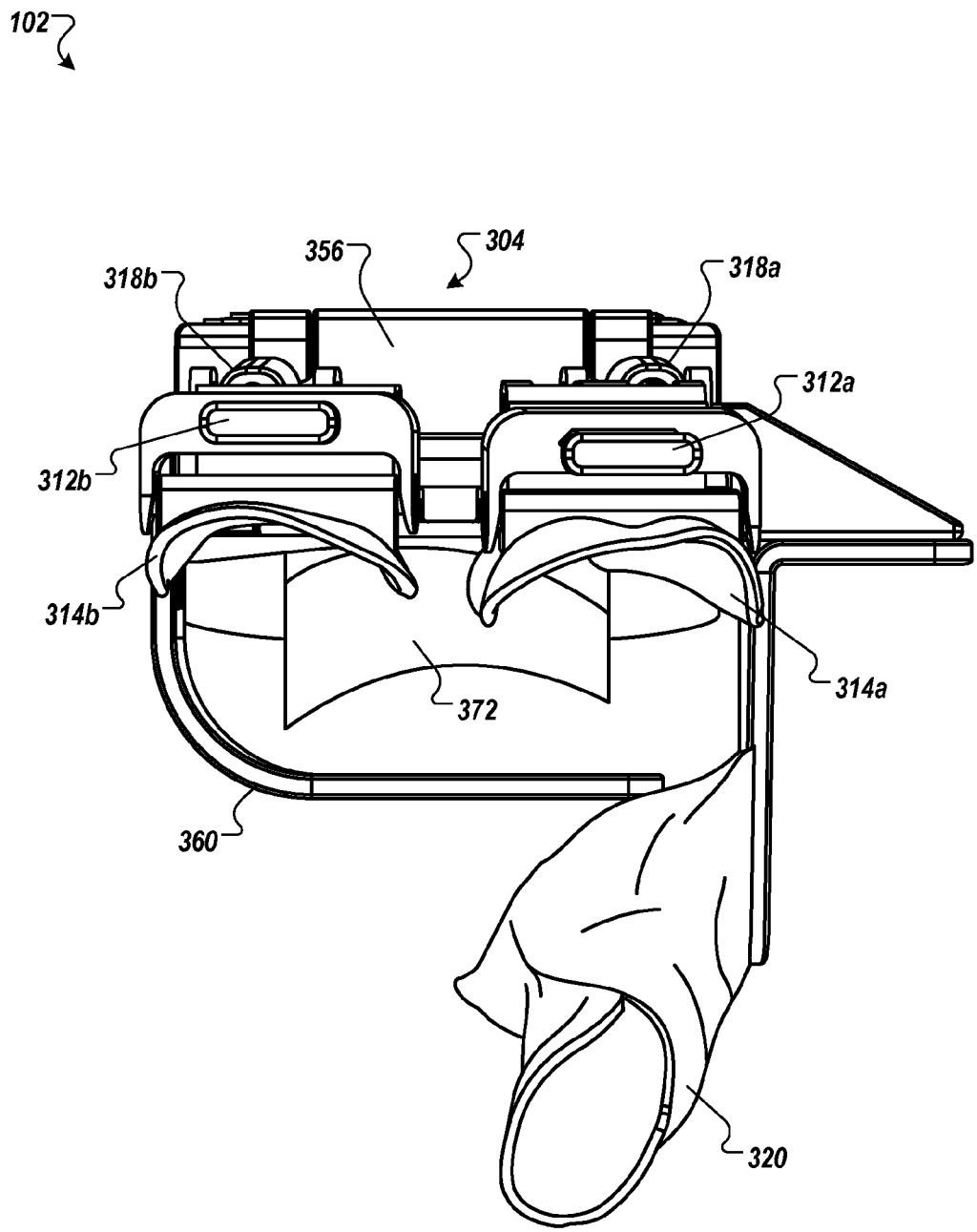

FIGS. 3-7 show more detail of the BCI/assist device 102 shown in FIG. 1A. Specifically, FIG. 3 is a top view of the device 102, FIG. 4 is a thumb-side view of the device 102, FIG. 5 is a bottom view, and FIG. 6 is a distal end view. FIGS. 7A and 7B show the device 102 being worn by a patient's forearm and hand, with the patient's hand being shown extended in FIG. 7A and closed in FIG. 7B. In general, the BCI/assist device 102 is sized and adapted to be positioned on top of a user's hand and forearm, with the user's fingertips exposed to allow tactile feedback. The BCI/assist device 102 may be made of durable, lightweight materials (e.g., plastic), and may be constructed using techniques such as factory-based machining or injection molding, factory-based or on-site 3D printing techniques, and/or other suitable manufacturing techniques.

Referring to FIGS. 3-7, the wearable BCI/assist device 102 includes a BCI component 104 and a body movement assistance component 108 operably connected to the BCI component 104 by way of a mechanical coupling mechanism (hinge) 310 and electrical connections contained within the mechanism coupling mechanism 310. The BCI component 104 is adapted and configured to be attached to the patient's forearm. The body movement assistance component 108 is adapted and configured to be worn generally by, and specifically on top of, the patient's hand (and in that sense, may be referred to as a glove). In general, the BCI/assist device 102 may be compact, lightweight, and with a low profile, such that the device 102 does not interfere with user activities. In some implementations, the BCI/assist device 102 may be modified according to a patient's physical deficit. As an example, if the patient has difficulty internally rotating or pronating the arm, the BCI component 104 (e.g., including a view screen) may be placed at a beveled angle, or at the side of the construct, reducing the need for rotation of the arm.

The BCI component 104 includes a housing 304 that has a generally rectangular box shape, wherein the housing 304 forms a chamber for housing the various internal components of the BCI component 104 (for example, the components of the BCI component 204 shown in FIG. 2). The BCI component housing 304 is sized such that it can be worn on the forearm of the patient. For example, the housing 304 may have a length (from proximal end 340 to distal end 342) of about six inches and a width (from the thumb side 344 of the housing 304 to the pinkie finger side 346 of the housing 304) of about three inches. The housing 304 includes a bottom panel 350, a top panel 352, a proximal end panel 354 (that is, the end positioned closest to the patient's shoulder), a distal end panel 356 (that is, the end positioned closest to the patient's hand), and two side panels 358 and 359 (namely, a thumb-side panel 358 and a pinkie finger side panel 359). These six panels 350, 352, 354, 356, 358 and 359 form the internal chamber that houses the internal components of the BCI component 104.

As shown best in FIG. 3, the top panel 352 of the housing 304 contains the display device 106. The display device 106 has a screen that is nearly as large as the top panel 352, or in other words, covers nearly the entire top surface of the BCI component 104. This display device 106 provides visual displays that can be easily viewed by the patient, owing to the positioning of the display device 106 when the BCI component 104 is worn as intended on the patient's forearm.

Figures 7A, 7B:
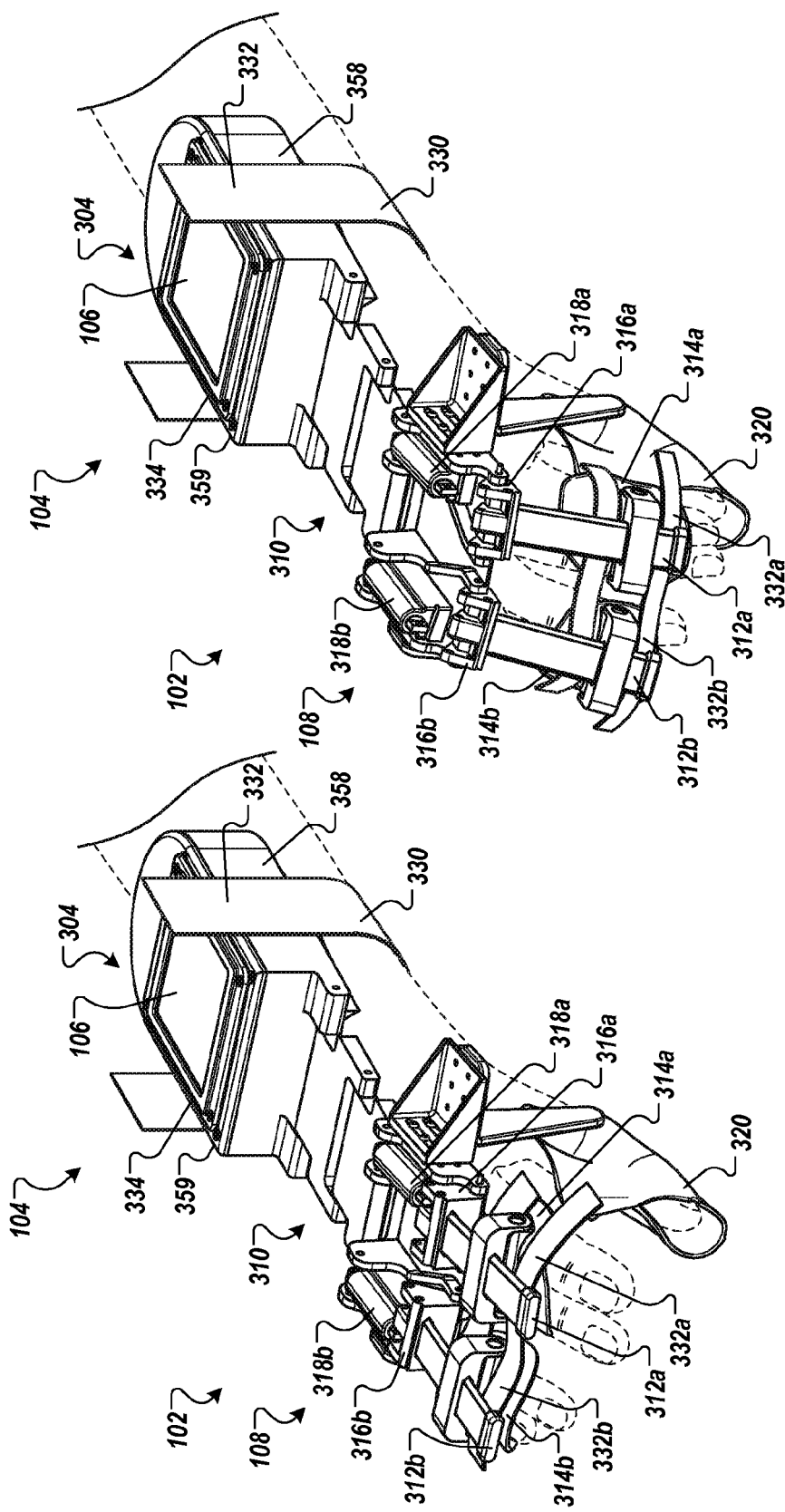
FIGS. 7A-7B are perspective diagrams of the wearable BCI/assist device shown in FIG. 1A in use on a patient's forearm and hand.

As shown best in FIGS. 4-6, the bottom panel 350 of the housing 304 rests on, and is secured to, a forearm bearing structure 370, the underside of which has a bearing surface 372 that generally conforms to the shape of the patient's forearm so that the BCI component 104 can rest securely on the patient's forearm. As such, the bearing surface 372 is generally straight in a longitudinal plane (as shown in FIGS. 4 and 5) and generally convex in an axial plane perpendicular to the length of the BCI component housing 304 (as shown in FIG. 6). The BCI component 104 also includes a flexible strap 330 so that the BCI component 104 can be strapped in place on the patient's forearm. This strap may be about 11-12 inches in length, and may have attachment mechanisms on each end (e.g., Velcro), wherein a first end 332 of the strap 330 is attachable to an outer surface of the thumb-side housing panel 358 and a second, opposite end 334 of the strap 330 is attachable to an outer surface of the pinkie finger side housing panel 359 (as shown in FIGS. 7A and 7B).

The body movement assistance component 108 (e.g., a component configured to be worn on a patient's right hand) can include a pair of finger group movement mechanisms 312a and 312b. The finger group movement mechanism 312a is attached to a finger group support mechanism 314a, which in turn can support a patient's index and middle fingers. Similarly, the finger group movement mechanism 312b is attached to a finger group support mechanism 314b, which in turn can support the patient's ring and pinky fingers. Each of the finger group movement mechanisms 312a and 312b in the present example has one active degree of freedom (e.g., flexure at the base) and two passive degrees of freedom (pad rotation and translation) and is connected to the body movement assistance component 108 by a respective finger group joint mechanism 314a and 314b. Each of the finger group joint mechanisms 314a and 314b, for example, can allow a finger joint range of motion ranging from zero degrees to about seventy degrees of flexion, and can include a mechanical stop to prevent finger hyperextension or bowing beyond zero degrees of extension. Although depicted as two finger group movement mechanisms 312a-b and two finger group support mechanisms 314a-b, other numbers and/or configurations of movement and support mechanisms are also possible. For example, four movement and support mechanisms may be used such that each movement mechanism corresponds to one of the patient's fingers. In some implementations, additional active and/or passive degrees of freedom may be added to each finger mechanism (e.g. metacarpophalangeal (MCP) yaw, MCP rotate, proximal interphalangeal (PIP) rotate, and distal interphalangeal (DIP) rotate).

The finger group support mechanisms 314a-b are slidably affixed to the finger group movement mechanisms 312a-b so as to slide longitudinally along the group movement mechanisms 312a-b. As depicted in FIG. 4, the group support mechanisms 314a includes a first portion 315a that is slidably affixed to the finger group mechanism 312a and a second portion 315b that is shaped and sized to support one or more of the patient's fingers and that is rotatably connected to the first portion 315a. The first portion 315a includes a hole that extends longitudinally through a front and back face of the first portion 315a, and that is shaped and sized to conform to the transverse shape and size of the group movement mechanism 312a. The hole in the first portion 315a may be sized and shaped to have a loose fit with the top and bottom surfaces of the finger group mechanism 312a so that the finger group support mechanism 314a has at least a threshold and limited degree of rotation (e.g., between 1 and 10 degrees) along a lateral axis of the group movement mechanism 312a. Such a limited degree of rotation for the finger group support mechanism 314a relative to a lateral axis of the group movement mechanism 312a can allow for variable movement of a patient's fingers outside of the specific range of motion defined by the finger group mechanism 312a. Other configurations for the first portion 315a of the group support mechanism 314a are also possible, such as through the use of brackets that are located on a top surface of the first portion 315a that slidably affix to tracks extending longitudinally along the sidewalls of the group movement mechanism 312a. As depicted in FIG. 4, the group movement mechanism 312a includes an enlargement at its distal end so as to stop the group support mechanism from sliding off of the longitudinal section of the group movement mechanism 312a.

The second portion 315*b* of the group support mechanism 314*a* is shaped and sized to fit one or more of a patient's fingers. In the depicted examples, the second portion 315*b* includes a curved surface that is shaped and sized to conform to the top of a patient's index and middle fingers. The second portion 315*b* can additionally include a mechanism to secure the group support mechanism 314*a* to the patient's fingers, such as the adjustable strap 332*a* depicted in FIGS. 7A-B. The second portion 315*b* can be connected to the first portion 315*a* in a manner that allows the second portion 315*b* to pivot along one or more axes relative to the first portion 315*a*. For instance, the second portion 315*b* is depicted in FIG. 4 as being hinged at the bottom of the first portion 315*a* so as to allow for the second portion 315*a* to pivot along a lateral axis relative to the group movement mechanism 312*a*. The pivoting of the second portion 315*b* relative to the first portion 315*a* can be limited (e.g., between 1 and 15 degrees). In some implementations, the second portion 315*b* is affixed to the first portion 315*a* in a manner that does not permit the second portion 315*b* to pivot or rotate.

The proximate ends of the finger group movement mechanisms 312*a-b* are rotatably affixed to finger group joint mechanisms 316*a-b* which permit the finger group movement mechanisms 312*a-b* to pivot along one or more generally lateral axes relative to the body of the BCI/assist device 102. The finger group movement mechanisms 312*a-b* may have a limited degrees of rotation based on the connections with the finger group joint mechanisms 316*a-b*, such as rotation ranging from a first position in which the finger group movement mechanisms 312*a-b* extends along a first plane that is generally parallel to the body of the BCI/assist device 102 to a second position in which the finger group movement mechanisms 312*a-b* extend along a second plane that is generally perpendicular to the body of the BCI/assist device 102. Other degrees of rotation are also possible, such as where the second position includes the finger group movement mechanisms 312*a-b* being at an acute angle relative to the body of the BCI/assist device 102.

To pivot each of the finger group movement mechanisms 312*a* and 312*b* about the respective finger group joint mechanisms 316*a* and 316*b*, the movement mechanisms 312*a* and 312*b* may each be controlled by a respective finger group position controller 318*a* and 318*b*. The finger group position controllers 318*a* and 318*b*, for example, can include motors and position feedback sensors. Thus, in addition to controlling the movement of supported finger pairs, the finger group position controllers 318*a* and 318*b* may detect movement and/or levels of force exerted by the patient's fingers. The finger group position controllers 318*a* and 318*b* can receive power and instructions from components included in the BCI component 104, for example, and can provide sensor data to the components. For example, the BCI component 104 can receive and analyze brain signals for a patient from the brain signal acquisition system 112. Based on the analysis of the patient's brain signals according to the techniques discussed in this document, the BCI component 104 can determine whether the patient demonstrated intent to move at least a portion of his/her hand through ipsilateral brain signals and, if such an intent is detected, can provide a signal to one or more of the finger group position controllers 318*a-b* to physically move the one or more of the patient's fingers.

Referring now to FIG. 4, a side view of the wearable BCI/assist device 102 is shown. The device 102 includes a thumb support mechanism 320 which can support the patient's thumb in a fixed position. In some implementations, the thumb support mechanism 320 may include a hinged component 321 which facilitates donning and removing of the device 102. For example, while the BCI/assist device 102 is being donned by a user, the thumb support mechanism may rotate about the hinged component 321. When the device 102 is worn, for example, the user may lock the hinged component 321. In some implementations, the thumb support mechanism 320 may be removable from the BCI/assist device 102. For example, a user may attach the finger group support mechanisms 314*a* and 314*b* separately from the thumb support mechanism 320, and may then attach (e.g., using a locking mechanism) the thumb support mechanism to the device 102. A hinged and/or removable thumb support mechanism 320, for example, may facilitate the donning and removal of the device 102 by patients with limited hand flexibility. The coupling mechanism 310 which attaches the body movement assistance component 108 to the BCI component 104 is shown as a hinged component which may allow flexion and extension of the patient's wrist.

FIGS. 5 and 6 show bottom and front views of the orthotic device, respectively. As shown best in FIG. 6, for example, a hand support mechanism 360 is shown for attaching a user's hand to the body movement assistance component 108. The hand support mechanism 360, can provide an opening for a user to don and remove the BCI/assist device 102, and can provide stability for the device while in use. In some implementations, the hand support mechanism 360 may be an adjustable strap that can permit the BCI/assist device 102 to be donned on the outside of a user's hand, which for a stroke patient may be clasped. Features of the BCI/assist device 102 may provide greater ease of use and operability to patients recovering from various impairments, such as a stroke or a traumatic brain injury. For instance, the hand support mechanism 360 being an adjustable strap, the finger group attachment mechanisms 332*a-b*, described below, being adjustable straps, and the hinged support component 321 for the thumb support mechanism 320 can permit the BCI/assist device to be donned on the outside of an user's hand first and then for each of the user's thumb and fingers to be individually positioned—in contrast to enclosed and finger and thumb supports which may require a user to guide his/her thumb and fingers into the supports as the device is being positioned on the user's hand.

FIGS. 7A and 7B are perspective diagrams which show the wearable BCI/assist device 102 in use. Referring to FIG. 7A, for example, the device 102 is shown as it may be worn by a patient, with the body movement assistance component 108 (e.g., a "glove" device) in an open position. For example, the BCI component 104 may be attached to the patient's forearm by a forearm attachment mechanism 330 (e.g., an adjustable strap). Similarly, the finger group support mechanisms 314*a* and 314*b* may be attached to the patient's index and middle fingers, and to the patient's ring and pinky fingers, respectively, by finger group attachment mechanisms 332*a* and 332*b* (e.g., adjustable straps). The patient's thumb may be supported in a fixed position by the thumb support mechanism 320.

Referring to FIG. 7B, for example, BCI/assist device 102 is shown as it may be worn by a patient, with the body movement assistance component 108 (e.g., a "glove" device) in a closed position. For example, each of the finger group position controllers 318*a* and 318*b* can cause the respective finger group movement mechanisms 312*a* and 312*b* to rotate about one or more axes defined by the rotatable connections with the respective finger group joint mechanisms 316*a* and 316*b*. As the finger group movement mechanisms 312*a* and 312*b* actively rotate (e.g., under the control of the device 102), for example, the respective finger group support mechanisms 314a and 314b may each passively slide toward the distal ends of the finger group movement mechanisms 312a and 312b, and may each passively pivot along a lateral axis relative to their respective group movement mechanisms to facilitate movement of each finger pair, causing the patient's hand to achieve a standard three jaw chuck pincer grip. By combining active and passive mechanisms for facilitating finger joint movement, for example, construction of the BCI/assist device 102 may be simplified while ensuring that a mechanical axis of rotation appropriately controls finger movement.

FIGS. 8A, 8B, 8C and 8D are flowcharts of example methods 800, 820, 840, and 860, for controlling a wearable BCI/assist device. In various implementations, the methods 800, 820, 840 and 860 may be performed by the systems 100, 200, and/or other systems not depicted, and are described below as being performed by the system 200 (shown in FIG. 2). Briefly, the method 800 includes an overall process for controlling a BCI/assist device including training, operation, and calibration modes, and including various conditions for transitioning between the modes. The example methods 820, 840 and 860 include processes for controlling the BCI/assist device while in training, general operation, and calibration modes, respectively.

Figure 8A:
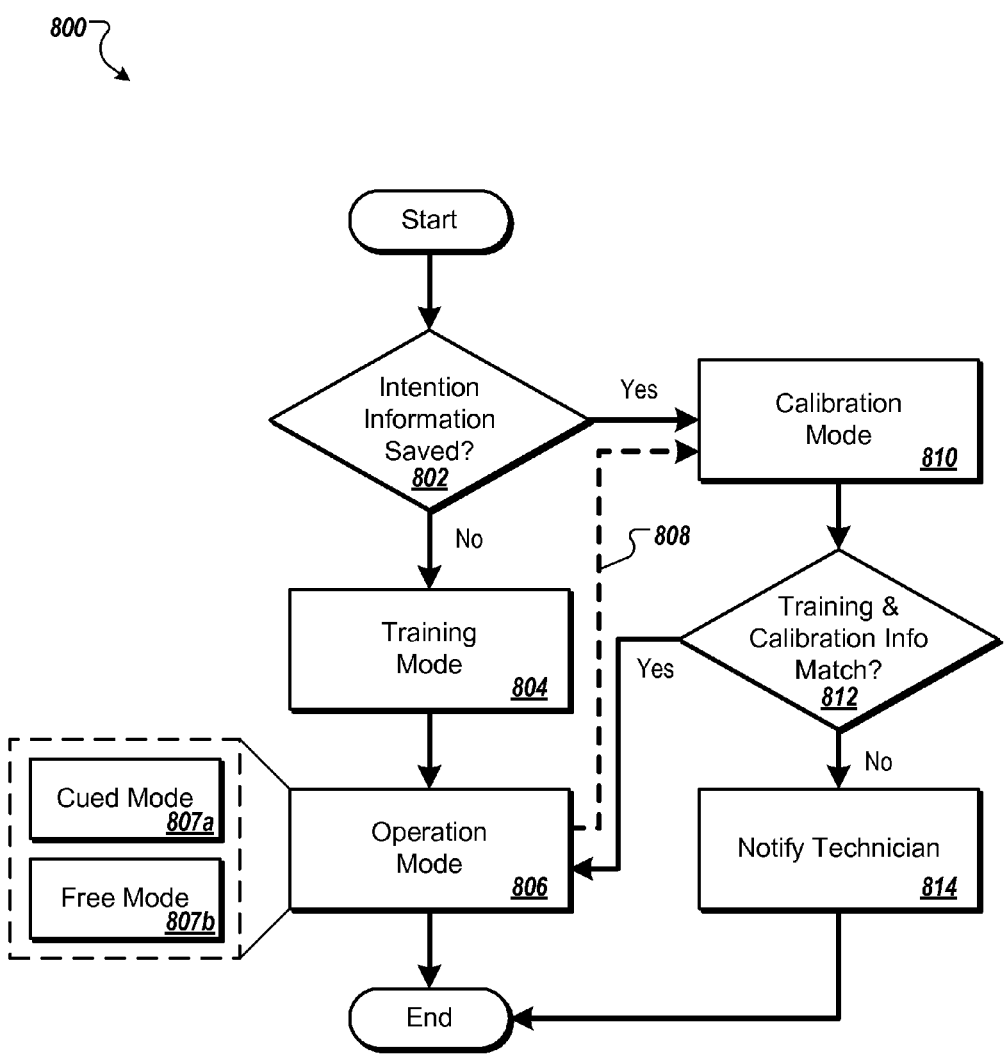
FIGS. 8A-8D are flowcharts of example methods performed by a BCI body movement assistance system.

Referring to FIG. 8A, the example method 800 for controlling a BCI/assist device starts at step 802, in which a determination is made of whether user intention information (e.g., brain signal features which may be used to control a BCI/assist device) has previously been saved. For example, when a user of the BCI/assist device 202 (shown in FIG. 2) powers the device on, the BCI component 202 can use the CPU 256 to execute program instructions for carrying out various processing functions. In general, when powering on, the BCI component 202 can reference the user intention information storage 264 (e.g., a data storage area for storing previously ascertained brain signals indicative of user intentions to perform various body movements) which may be stored in the device's non-volatile memory 260 to determine whether the device has been configured. If user intention information has not previously been saved (e.g., upon initial use, after a device memory wipe, etc.), for example, the BCI/assist device 202 can enter a training mode at step 804.

In general, during a training mode (step 804), the BCI/assist device 202 can prompt/cue a user (e.g., a patient) to perform various actions (e.g., moving one or both hands, holding one or both hands still, resting, etc.). To prompt the user, for example, the BCI component 204 can provide visual prompts (e.g., through the display equipment 206) and/or acoustic prompts (e.g., through the audio output equipment 294). As the user performs a prompted action, the BCI/assist device 202 can receive the user's neural signal data 240 from the brain signal acquisition system 212, for example. The neural signal data 240 may be used for identifying user intention information (e.g., control features) that will subsequently be used by the BCI/assist device 202 in a general operation mode.

After the training mode process has been performed, the BCI/assist device 202 may enter a general operation mode at step 806. In general, during the general operation mode (step 806), the brain signal acquisition system 212 can collect neural signals from the electrodes 214, and can provide neural signal data 240 to the BCI/assist device 202. The BCI component 204 can use the neural signal interpreter 270, for example, to determine movement intentions of the user, based on the saved user intention information 264. For example, the neural signal interpreter 270 can identify one or more features of the neural signal data 240 (e.g., electrode location, frequency, amplitude, etc.) that correspond with a set of features that have been previously correlated with a particular body movement intention. The BCI component 204 can then reference the body motion range parameter settings 268 to identify a range of motion for the body movement assistance component 208 that is associated with the movement intentions of the user (e.g., to open or close a hand). Using the motion range parameter settings 268, for example, the device control module 272 can drive one or more of the motors 282, thereby moving one or more of the movable components 284 a suitable distance.

The operation mode 806 can include one or more different types of sub-operations, such as a cued mode of operation (807a) and/or a free mode of operation (807b). During the cued mode of operation (807a), a patient can be cued/prompted to perform specific actions, such as moving a particular part of his/her body and/or resting for a period of time. The cues/prompts that are provided during the cued mode of operation (807a) can be visually output on a display and/or audibly output using one or more speakers. The cued mode of operation (807a) can persist for at least a threshold period of time and/or at least a threshold number of actions when the operation mode 806 is entered so as to ensure a minimum amount of rehabilitation time and/or repetitions for the patient. The parameters of the cued mode of operation (e.g., length of time, number of repetitions) may be predetermined (e.g., set by a technician) and/or may be dynamically determined based on the patient's progress to date and a prescribed therapy schedule for the patient.

The operation mode 806 can additionally and/or alternatively include the free mode of operation (807b) which can allow a patient to freely operate a BCI/assist device without specific cues or prompts. For example, during the free mode of operation (807b) a patient can provide input through the brain signal acquisition system 212 to cause the BCI/assist device 202 to perform various actions, such as opening and/or closing the BCI/assist device described with regard to FIGS. 3-7. Free mode can permit a patient to use the BCI/assist device 202 to perform daily tasks in the context of the patient's daily life, which, as described above, can increase the effectiveness of rehabilitation for the patient. A patient may have to periodically (e.g., twice a day, once a day, once every two days, weekly) complete the cued mode of operation (807a) before being permitted to enter the free mode of operation (807b).

If, at step 802, a determination is made that user intention information 264 has previously been saved, for example, the BCI/assist device 202 can enter a calibration mode at step 810. In general, during the calibration mode (step 810), the user's neural signal data 240 can be received from the brain signal acquisition system 212, and can be used to generate calibration data 266, which can be used to define a physiological baseline from which relative control features (e.g., sets of previously ascertained brain signals indicative of a user intention to perform particular body movements) can be identified. At step 812, a determination is made of whether the user intention information identified during the training mode (step 804) matches the information identified during the calibration mode (step 810). If the user intention information 264 identified during the training mode matches the user intention information identified from the calibration data 266, for example, the BCI/assist device 202 can enter the general operation mode at step 806. If the user intention information 264 identified during the training mode does not match the user intention information identified from the calibration data 266, for example, a technician (e.g., a health care provider, a physical therapist, etc.) can be notified at step 814.

In some implementations, a BCI/assist device can enter a calibration mode from a general operation mode. For example, as shown by arrow 808, the BCI/assist device 202 can enter the calibration mode (step 810) directly from the general operation mode (step 806). While using the BCI/assist device 202 in general operation mode, for example, a device user may interact with the display equipment 206 (e.g., a touch screen) and/or one or more input devices 292 (e.g., buttons) to reset or restart the device, effectively switching the device to calibration mode. Such an action may be performed by the user to troubleshoot the device if it performs inadequately in general operation mode, for example.

Figure 8B:
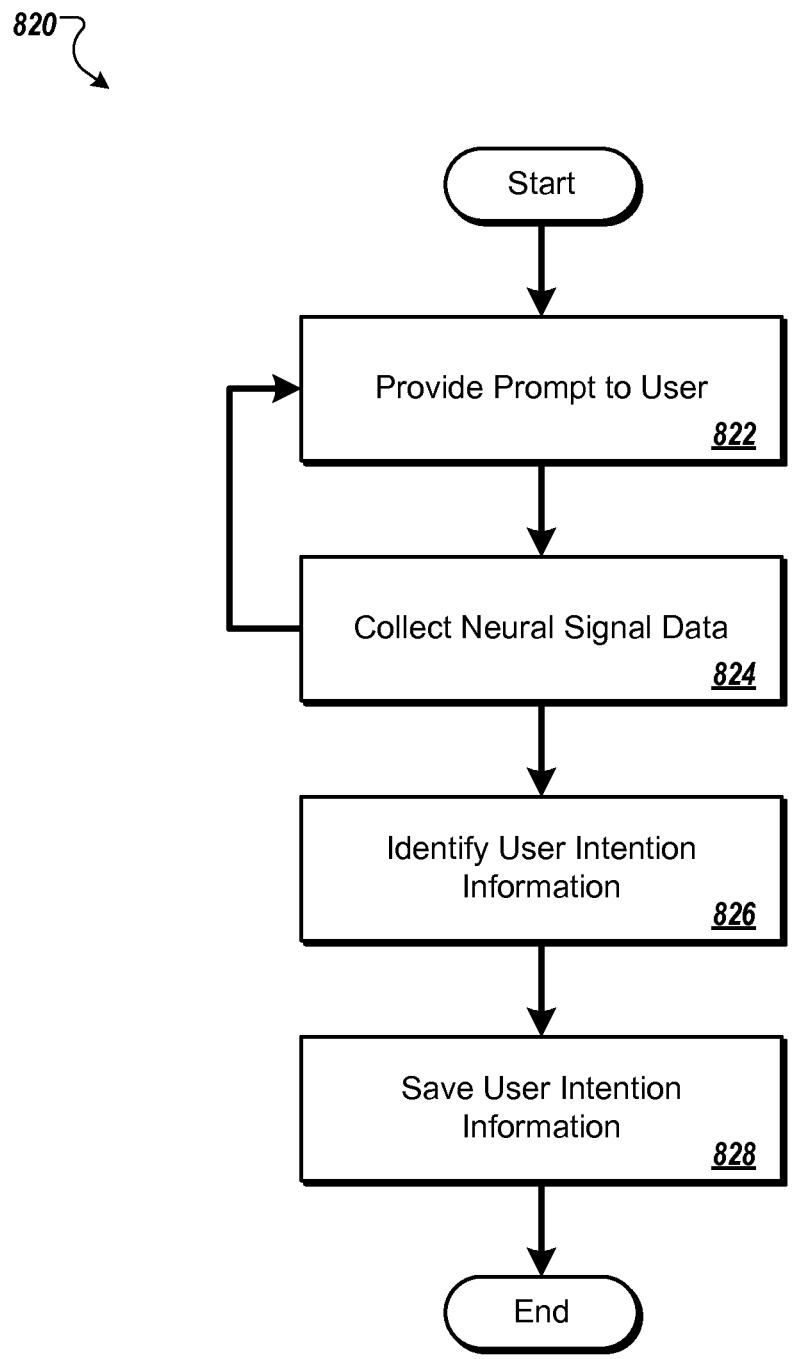

Referring to FIG. 8B, the example method 820 for controlling a BCI/assist device while in training mode (e.g., step 804 of the method 800) is depicted. To perform the method 820, for example, the BCI/assist device 202 (shown in FIG. 2) can use the CPU 256 to execute computer application code associated with the training mode module 274. In general, the method 820 includes steps for providing prompts to a user, collecting neural signal data, identifying control features based on the neural signal data, and saving the control features for subsequent use.

The method 820 starts at step 822, by providing a prompt to a user. For example, the BCI/assist device 202 (shown in FIG. 2) can provide visual prompts (e.g., through the display equipment 206) and/or acoustic prompts (e.g., through the audio output equipment 294), and/or tactile prompts (e.g., through the tactile devices 281) to direct the device user through a series of actions. In general, prompts may include instructions for moving various body parts (e.g., impaired and/or unimpaired body parts) and for holding the body parts still. For example, the user may be prompted to open or close one or both hands, hold one or both hands still, and so forth.

As the prompt is presented and while the user attempts the prompted action, neural signal data can be collected at step 824. For example, the brain signal acquisition system 212 can use the electrodes 214 to collect to collect the user's brain signals as the user perceives the prompted instructions, plans to execute the instructions, and attempts the instructed movement. Neural signal data 240 (e.g., electrode location, frequency, amplitude, etc.) can be provided by the acquisition system 212 to the BCI/assist device 202 through the respective connection interfaces 252 and 250. As the BCI/assist device 202 receives the neural signal data 240, for example, the device can track the data relative to the time of prompt presentation and can correlate and store the data using the volatile memory 258 and/or the non-volatile memory 260.

A training mode data collection process including steps 822 (providing a prompt to a user) and 824 (collecting neural signal data) may be performed iteratively. For example, a predetermined series of prompts can be provided, and corresponding neural signal data can be collected for each of the prompts in the series. In some implementations, a training mode data collection process may be performed for a predetermined series of prompts and/or a predetermined period of time (e.g., an hour, thirty minutes, ten minutes, etc.). In some implementations, prompts may be provided in a random series. For example, each prompt in a series of prompts can be randomly cued such that a user's attention to the prompts is encouraged, and that responses may be distinguished from prompts. In some implementations, a series of prompts may be adaptively presented, based on previously received signal data. For example, if the BCI/assist device 102 does not receive enough data to distinguish an ipsi versus contra signal, the device can continue to cue and prompt until one or more signals become statistically significant. As another example, prompts for increasingly complex movements may be presented during the series. For example, once the BCI/assist device 102 is able to distinguish ipsi hand from contra hand, it may then provide prompts for distinguishing ipsi thumb against contra thumb, then ipsi index finger versus contra index finger, and so forth.

User intention information can be identified at step 826. When the training mode data collection process is completed, for example, the BCI/assist device 202 can provide collected data to the central management computing system 220 through the network 230, using the communications module 279, and using the connection interfaces 250 and 254, respectively. As another example, the BCI/assist device 202 can use the communications module 279 to continually provide data to the central system 220, as the data is collected. As another example, the central system 220 can periodically request (e.g., poll) the BCI/assist device 202 for data through a web-based interface or another suitable technique. Upon receiving the collected data, for example, the central system 220 can provide the data to the device usage analyzer 222. For example, the device usage analyzer 222 can pre-process the prompt presentation and neural signal data collected during the training mode data collection process to reduce noise and to assist a technician in selecting optimal montage and weighting attributes (e.g., control features) for use by the BCI/assist device 202 during a general operation mode. In some implementations, the weighting attributes are automatically selected by the device usage analyzer 222 and without direct input from a technician.

User intention information can be saved at step 828. For example, a technician can use the rehabilitation management module 224 to configure the BCI/assist device 202. Device configuration data may include montage and weighting attributes (e.g., control features), and may include other device usage and rehabilitation session parameters. For example, device usage and rehabilitation session parameters may include information related to assisted body parts (e.g., a body part's range of motion, whether a BCI/assist device is to assist a right or left hand, etc.), default operating states (e.g., whether a glove is to be in a normally open or closed position), rehabilitation sessions (e.g., types of motions to be performed, target numbers of motions to be performed per session or per day, etc.), device control parameters (e.g., an amount of time a BCI/assist device may be idle before powering off, an amount of time after which a BCI/assist device is to be retrained or recalibrated, a frequency for sending device GPS location information to a remote system, device memory reset instructions, etc.), and other suitable parameters. Such device usage and/or rehabilitation session information can be used in a variety of ways, such as to enhance the compliance requirements for a patient with a treatment regime (e.g., increase period and/or number of repetitions for cued control mode before entering free mode of operation) and/or to increase the complexity of a treatment regime for a patient with documented good performance. After the montage and weighting attributes and other parameters are defined for use by the BCI/assist device 202, for example, the central management system 220 can provide configuration updates to the device through the network 230, using the connection interfaces 254 and 250, and using the communications module 279. Upon receiving the configuration updates, for example, the BCI component 204 can save the updates in non-volatile memory 260 as user intention information 264, motion parameters 268, and device parameters 262.

Figure 8C:
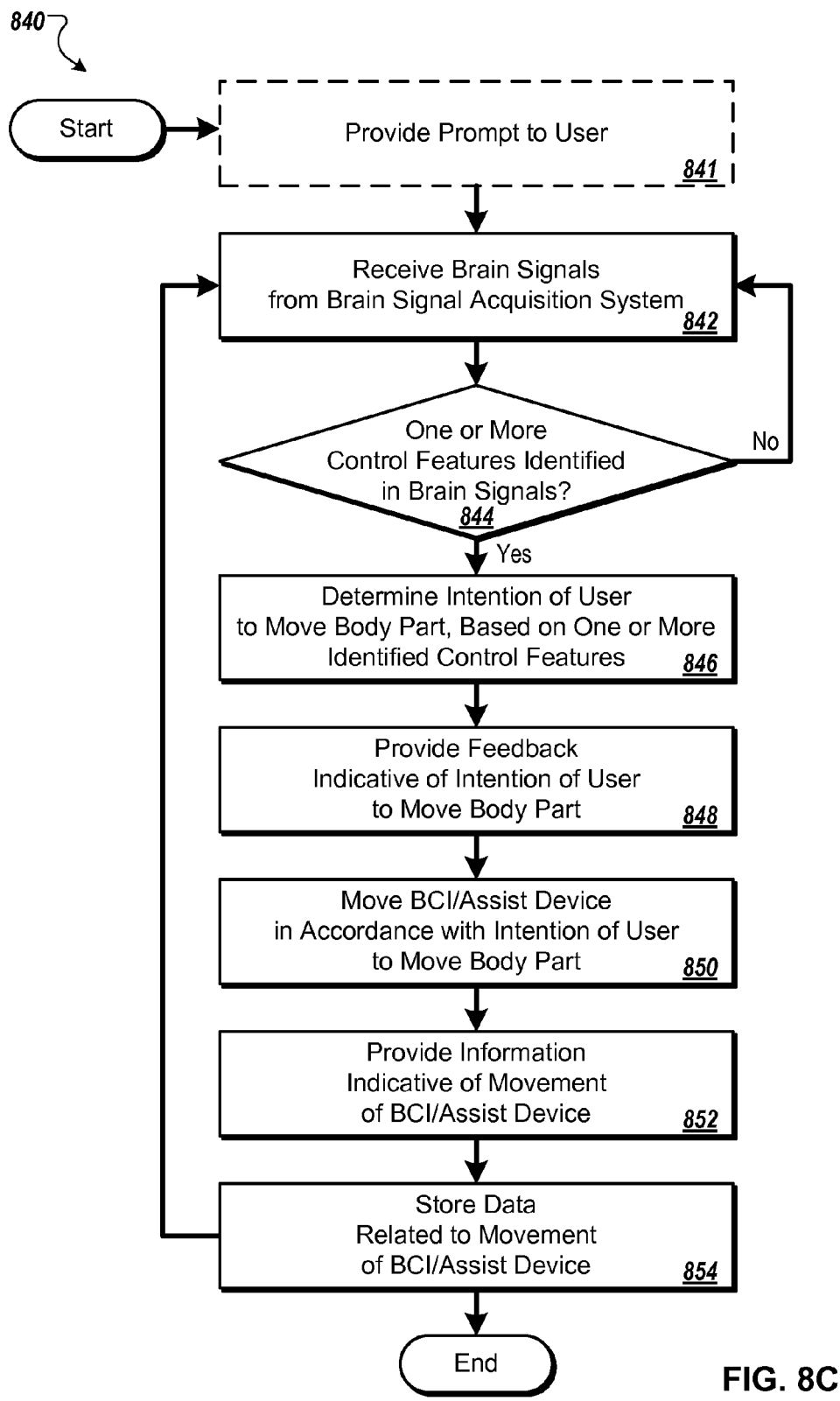

Referring to FIG. 8C, the example method 840 for controlling a BCI/assist device while in general operation mode (e.g., step 806 of the method 800) is depicted. To perform the method 840, for example, the BCI component 204 (shown in FIG. 2) can use the CPU 256 to execute computer application code associated with the operational mode module 278. In general, the method 840 includes steps for optionally prompting a user to perform an action, receiving brain signals from a signal acquisition system, determining an intention of the user to move a body part (based on previously identified control features), displaying information indicative of the determined intention, moving a body movement assistance component in accordance with the determined intention, displaying information indicative of the device movement, and storing data related to the device movement.

The method 840 starts at step 841, by optionally providing a prompt to a user. As described above, operation modes may include a cued mode of operation (807a) and a free mode of operation (807b). During the free mode of operation (807b), for example, a patient can use the BCI/assist device 202 to perform tasks in the context of the patient's daily life, without receiving prompts to perform particular actions. During the cued mode of operation (807a), for example, a patient can be cued or prompted to perform specific actions as part of a therapy session. For example, during the cued mode of operation, the BCI/assist device 202 (shown in FIG. 2) can provide visual prompts (e.g., through the display equipment 206) and/or acoustic prompts (e.g., through the audio output equipment 294) and/or tactile prompts (e.g., through the tactile devices 281) to direct the device user through a series of actions. As described below, in some implementations the patient may interact with a user interface to indicate whether a BCI/assist device is to operate in a cued mode or a free mode.

At step 842, the BCI/assist device 202 can receive brain signals from the signal acquisition system 212. For example, the brain signal acquisition system 212 (e.g., a headset) can use the electrodes 214 to collect the user's brain signals, and neural signal data 240 (e.g., electrode location, frequency, amplitude, etc.) can be provided by the acquisition system 212 to the BCI/assist device 202 through the respective connection interfaces 252 and 250. Upon receiving the neural signal data 240, for example, the BCI component 204 can determine at step 844 whether one or more control features are identified in the brain signals that are indicative of a user intention to perform a predefined body movement (e.g., an opening or closing of a hand). For example, the BCI component 204 can use the neural signal interpreter 270 to analyze the neural signal data 240 and to identify corresponding user intention information 264 which had been identified and saved while the device previously operated in training mode. In general, analyzing the neural signal data 240 can include signal processing techniques for correlating an electrode pattern (i.e., signal frequency and magnitude at each electrode) and sequence (i.e., progress over a short segment of time) with a particular intention. If the BCI/assist device 202 does not identify corresponding intention information, for example, the device can continue receiving and analyzing neural signal data 240, and can monitor the data for signal changes.

When the BCI/assist device 202 identifies one or more control features in the received brain signals, at step 846 the device can determine an intention of the user to move a body part, based on the control features. In general, for each pattern and sequence of brain signals that have been identified, a corresponding control signal may be identified. For example, when the neural signal interpreter 270 identifies one or more control features in the neural signal data 240 that match one or more of the previously identified and saved user intention information 264, the neural signal interpreter 270 can identify a user movement intention (e.g., an opening or closing of a hand) associated with the matching control features.

In some implementations, a determination of an intention of the user to move a body part may be based at least in part on feedback from one or more device sensors. For example, the BCI/assist device 202 can include pressure sensors at locations of possible contact between the BCI/assist device 202 a patient and/or external objects (e.g., objects that the BCI/assist device 202 grabs/holds). Such sensors could be used to ensure safe operation of the BCI/assist device 202 for both the patient and the environment within which the BCI/assist device 202 is being used. For instance, pressure sensors could be used to ensure that the force exerted by the BCI/assist device 202 does not exceed a maximum threshold level and/or so as to minimize spikes in the application of force (e.g., ensure uniform application of force throughout a task). In another example, the BCI/assist device 202 can use one or more position sensors that can detect the presence of parts of a patient's body (e.g., fingers, hand, joints, and/or muscles). Such position sensors can be used to identify instances when the BCI/assist device 202 is not properly position on a patient's body and to suggest corrective action to the patient, so as to ensure safe and comfortable operating conditions. For example, based on feedback from the sensors 280 (e.g., pressure and/or joint position sensors), the body movement assistance component 208 can detect possible movement and/or resistance of the user. Data provided by the sensors 280, for example, may be used in conjunction with movement intentions identified by the neural signal interpreter 270 to control the BCI/assist device 202.

At step 848, the BCI/assist device 202 can provide feedback indicative of the user's intention to move a body part. For example, the BCI component 204 can present visual feedback (e.g., using the display equipment 206) and/or acoustically feedback (e.g., using the audio output equipment 294) and/or tactile feedback (e.g., using the tactile devices 281) related to the intention. In some implementations, the feedback may include a visually and/or acoustically presented phrase (e.g., "open hand", "close hand", etc.). In some implementations, the feedback may include vibrotactile feedback to a body part (e.g., a hand or finger) associated with the intention. In some implementations, the feedback may include a representation of the user's intention to move a body part to a particular position in a range of possible positions and/or to move the body part with a particular amount of force or speed. For example, the display 206 can present a graphical representation of a hand in one of a range of positions, ranging from a fully closed fist, to a partially open hand, to a fully open hand. As another example, the display 206 can present one or more numerical values, graphics, colors, or other suitable indicators of position, force, or speed.

At step 850, the BCI/assist device 202 can move in accordance with the user's intention to move the body part. For example, the device control module 272 can receive user movement intention information from the neural signal interpreter 270 and can reference the body motion range parameter settings 268 to determine appropriate corresponding movements of the body movement assistance component 208. Based on the determined movements, for example, the BCI component 204 can use the device control module 272 to drive one or more of the motors 282, thereby moving one or more of the movable components 284. For example, a glove device (e.g., the body movement assistance component 108, shown in FIG. 1A) can open, based on the user's intention to open his or her hand, and/or can close, based on the user's intention to close the hand. The motion of the glove device, for example, may be limited by a device controller (e.g., the device control module 272), based on appropriate joint positions. In some implementations, the body range parameter settings 268 may be configured for a particular user. For example, a distance, speed, and/or force to be applied to the movable components 284 for a particular type of movement (e.g., the opening or closing of a hand) may vary between users, and may be tailored for each user by a technician.

At step 852, the BCI/assist device 202 can provide information indicative of device movement. For example, the BCI component 204 can present device movement information visually (e.g., using the display equipment 206) and/or acoustically (e.g., using the audio output equipment 294). In some implementations, device movement information may include information indicative of the completion of a particular type of movement. For example, a BCI component of an orthotic glove device (e.g., the BCI component 104, shown in FIG. 1A) can present an indication (e.g., visual and/or acoustic) of the completion of a glove opening, a glove closing, and so forth. In some implementations, device movement information may include information indicative of a cumulative number of device movements during a session or day. For example, the BCI component 204 can display a target number of movements to be performed by a user per session or per day, and a cumulative number of movements actually performed by the user.

At step 854, the BCI/assist device 202 can store data related to movement of the device. For example, upon completion of a particular movement (e.g., a movement cycle starting at a fully closed glove position, proceeding to a fully open glove position, and returning to a fully closed glove position), the BCI component 204 can increment a counter associated with the movement, and can store an updated value for the counter as usage information 269 included in non-volatile memory 260. In some implementations, the BCI component 204 may store additional usage information 269 associated with a completed movement, such as a time of day the movement was completed, an elapsed time to complete the movement, and other related information.

While in general operation mode, for example, the BCI/assist device 202 may continually monitor received neural signal data 240 for changes, and may continually move one or more movable components 284 based on identified movement intentions. In general, identified movement intentions may be translated to device movement commands about twenty times per second. System delay during use, for example, may be less than one hundred and fifty milliseconds between the time of brain signal detection and device movement. Thus, the BCI/assist device 202 may be used for rehabilitative purposes and may be used in a free control mode for general robotic assistance, thus providing the therapeutic benefit of facilitating a patient's use of an affected body part to accomplish regular tasks in a regular setting (e.g., the patient's home). If the device performs inadequately during the general operation mode, for example, the user (or a technician) may switch the device to calibration mode.

Figure 8D:
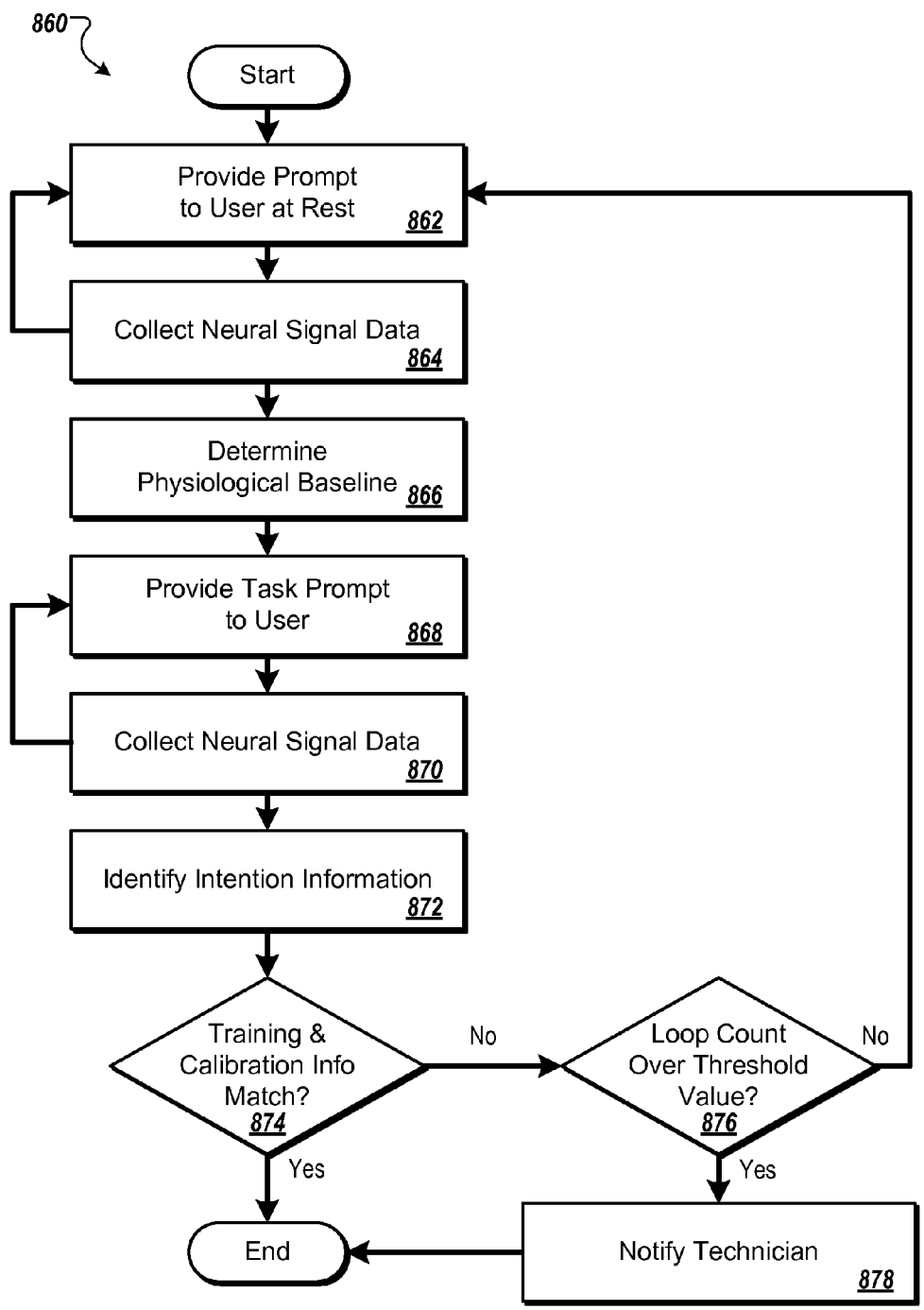

Referring to FIG. 8D, the example method 860 for controlling a BCI/assist device while in calibration mode (e.g., step 810 of the method 800) is depicted. To perform the method 860, for example, the BCI component 204 (shown in FIG. 2) can use the CPU 256 to execute computer application code associated with the calibration mode module 276. In general, the method 860 includes steps for providing prompts to a user, collecting neural signal data, identifying intention information based on the neural signal data, and determining whether the identified intention information matches previously identified intention information. Calibration mode may generally be used after the successful completion of a training mode process (e.g., the example method 820), and may define a new baseline physiology to identify an appropriate level of control to be used during a subsequent general operation mode (e.g., the example method 840).

The method 860 starts at step 862, by providing a prompt to a user at rest. For example, the BCI component 204 (shown in FIG. 2) can provide visual prompts (e.g., through the display equipment 206) and/or acoustic prompts (e.g., through the audio output equipment 294) and/or tactile prompts (e.g., through the tactile devices 281) associated with a series of actions. In general, the prompts may be related to the movement or resting of various body parts (e.g., moving one or more hands, holding one or more hands still, etc.), however, in some implementations, the prompts presented during a calibration mode may include directions for moving and resting only an affected body part. While viewing and/or hearing the prompts, for example, the user may remain at rest—that is, the user perceives but does not attempt to perform the corresponding actions of movement-related prompts during step 862.

As the prompt is presented and while the user remains at rest, neural signal data can be collected at step 864. For example, the brain signal acquisition system 212 can use the electrodes 214 to collect to collect the user's brain signals as the user perceives the prompted instructions. Neural signal data 240 (e.g., electrode location, frequency, amplitude, etc.) can be provided by the acquisition system 212 to the BCI/assist device 202 through the respective connection interfaces 252 and 250. As the BCI component 204 receives the neural signal data 240, for example, the calibration mode module 276 can generate associated calibration data 266. At step 866, the BCI component 204 can use the calibration data 266 collected and generated during steps 862 and 864 to establish a physiological baseline of the user to be subsequently used in determining user intent.

A baseline determination process including steps 862 (providing a prompt to a user at rest) and 864 (collecting neural signal data) may be performed iteratively. For example, a series of prompts can be provided, and corresponding neural signal data can be collected for each of the prompts in the series. In some implementations, a baseline determination process may be performed for a predetermined series of prompts and/or a predetermined period of time (e.g., two minutes, a minute, thirty seconds, etc.).

The method 860 continues at step 868, by providing a task prompt to a user. For example, the BCI component 204 can provide visual and/or acoustic and/or tactile prompts to direct the device user through a series of actions. In general, task prompts may include instructions for moving various body parts (e.g., impaired and/or unimpaired body parts) and for holding the body parts still. For example, the user may be prompted to continually move one or both hands, to hold one or both hands still, to not move any parts of the body, and so forth. Examples of visual prompts that are provided to the user are depicted in FIGS. 9A-F, as described below.

As the prompt is presented and while the user attempts to perform the prompted action, neural signal data can be collected at step 870. For example, the brain signal acquisition system 212 can use the electrodes 214 to collect to collect the user's brain signals as the user perceives the prompted instructions, plans to execute the instructions, and attempts the instructed movement. Neural signal data 240 (e.g., electrode location, frequency, amplitude, etc.) can be provided by the acquisition system 212 to the BCI/assist device 202 through the respective connection interfaces 252 and 250. As the BCI component 202 receives the neural signal data 240, for example, the device can generate associated calibration data 266.

A calibration mode data collection process including steps 868 (providing a task prompt to a user) and 870 (collecting neural signal data) may be performed iteratively. For example, a series of prompts can be provided, and corresponding neural signal data can be collected for each of the prompts in the series. In some implementations, a calibration mode data collection process may be performed for a predetermined series of prompts (e.g., 30 trials, 50 trials, etc.) and/or a predetermined period of time. Intention information can be identified at step 872. When the calibration mode data collection process is completed, for example, the BCI component 204 can use the calibration mode module 276 to compare signals collected during the baseline determination process and during the calibration mode data collection process. Intention information, for example, can be based on signals that are statistically significant in terms of electrode location, frequency, and amplitude change. At step 874, a determination is made of whether the intention information previously identified during the training mode matches the intention information identified during the calibration mode. A variety of techniques can be used to determine whether the intention information from the training mode and the calibration mode match, such as determining whether signals from the same electrode and frequency band have the same statistically significant changes. If such similar statistically significant changes are detected, then the intention information from the training mode and the calibration mode can be determined to match. If the intention information identified during the training mode matches the intention information identified during the calibration mode, for example, the BCI/assist device 202 can proceed to the general operation mode. If the intention information identified during the training mode does not match the intention information identified during the calibration mode, for example, the BCI component 204 can increment a loop counter and can determine whether the loop counter is over a threshold value (e.g., two, three, four, or another suitable value) at step 876.

If, at step 876, the loop counter is at or under the threshold value, the calibration mode process can be repeated. If, however, the loop counter is over the threshold value, a technician (e.g., a health care provider, a physical therapist, etc.) can be notified at step 878. For example, the BCI component 204 can provide a visual and/or acoustic prompt to the user to contact the technician. As another example, the BCI component 204 can provide notification data to the central management system 220 through the network 230, using the communications module 279, and using the connection interfaces 250, and 254, respectively.

While performing any of the example methods 800, 820, 840, or 860, for example, the BCI/assist device 202 may provide device status and operation error information to the user. For example, if an operation error (e.g., faulty communication with the brain signal acquisition system 212 and/or the central system 220, the failure of one or more hardware or software components, etc.) occurs, the BCI component 204 can provide error information to the user through the display equipment 206. As another example, power status information (e.g., a battery charge level, a charging indicator, etc.) can be provided through the display 206. In some implementations, operation error detection may include techniques for providing prompts and providing feedback. During a calibration mode, for example, a prompt can occasionally (and intentionally) be provided, and the BCI/assist device 202 can perform in a manner opposite of what would be expected by a user; such a condition can create error signals that may be manifested as a central increase in theta or a P300 response. As another example, a data driven approach can be used, such that a particular signal (electrode, frequency, amplitude, phase, etc.) may be present when the user's BCI/assist device 202 performs an unexpected action. The "error signals", for example, can then be used to calibrate or detect need for recalibration if error signals (e.g., a number or frequency of error signals) are detected during the free use mode. Device status, operation error, and usage information (e.g., a history of motions performed by the device user per session or per day, a history of power on/off times, etc.) may be periodically or continually provided to the central system 220.

Referring now to FIGS. 9A through 9D, there are shown an example series of display screens of an instance of a graphical user interface (GUI) for prompting a user (e.g., a patient) during a training mode (e.g., training mode 804) data collection process (e.g., method 820 described with regard to FIG. 8B) and/or during a calibration mode (e.g., calibration mode 810) data collection process (e.g., method 820 described with regard to FIG. 8D). A user interface 900a may be visually presented to the user by display equipment included in a BCI/assist device. For example, the user interface 900a may be presented by the display device 106 of the BCI/assist device 102 (shown in FIG. 1), or by the visual output display equipment 206 of the BCI/assist device 202 (shown in FIG. 2).

In general, prompts may include instructions to a patient to move and/or rest (not move) impaired and/or unimpaired body parts. While the user responds to the prompts, brain signal data may be collected and may be used for various purposes, such as for determining whether the patient is a suitable candidate for using a BCI/assist device, for identifying brain signals associated with intentions to move body parts, and/or for identifying a patient's physiological baseline at the beginning of a therapy session. Upon powering on a BCI/assist device, for example, the patient may be visually and/or acoustically presented with initial instructions for using the device, such as instructions to remain seated and relatively still during a screening session or a calibration session.

Figure 9A:
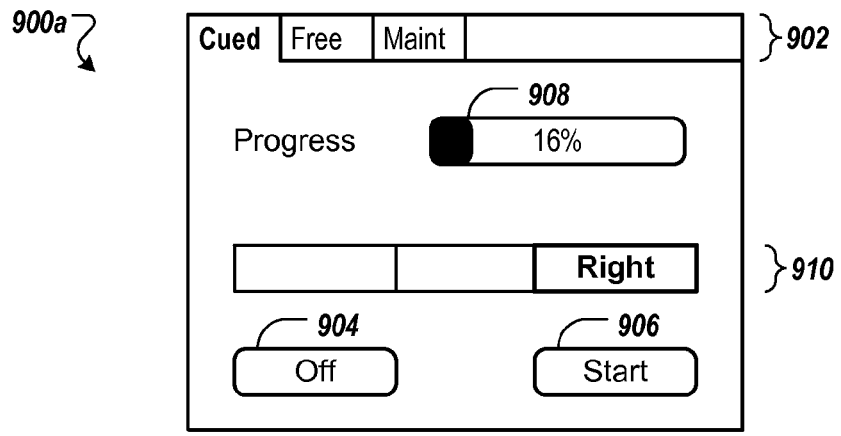
FIGS. 9A-9G are diagrams of example user interface displays that may be provided by a wearable BCI/assist device.

Referring to FIG. 9A, the user interface 900a includes a mode selection control 902, a power control 904, and a start control 906. The controls 902, 904, and 906, for example, may be touch screen controls, or may correspond to physical buttons (e.g., a keypad) of a wearable BCI/assist device (e.g., the BCI/assist device 102). In the present example, the mode selection control 902 indicates that the BCI/assist device 102 is currently in a "cued" mode, and that the patient is to perform various actions in response to prompts presented by the device. The patient can select the start control 906, for example, to instruct the BCI/assist device 102 to begin presenting a series of prompts associated with a training session or a calibration session. The patient can select the power control 904, for example, to turn off the BCI/assist device 102 during training or calibration sessions, if desired.

During a device training or calibration session, for example, a BCI/assist device can present information related to the progress of the session. For example, the user interface 900*a* includes a progress indicator 908 for providing information to a patient, indicative of a portion of the session that has been completed relative a portion of the session that has yet to be completed. The progress indicator 908, for example, may include numerical information (e.g., a "percentage complete", a "stage X of Y complete", etc.) and/or graphical information (e.g., a progress bar). As the patient follows the device's prompted instructions during a training or calibration session, for example, the progress indicator 908 can be updated on the user interface 900*a* so that the patient may be continually apprised of the session's progress.

The user interface 902*a* can include a prompt presentation area 910. In general, prompts may include visual and/or acoustic cues for a patient to move impaired and/or unimpaired body parts (e.g., hands) individually or simultaneously, and may include cues for the patient to rest. For example, when prompted to move a hand the patient can move (or imagine moving) his or her fingers continually—such as by moving (or imagining to move) each finger of a hand sequentially to touch his or her thumb. In some implementations, each prompt in a series of prompts may be presented by the BCI/assist device 102 for a predetermined amount of time (e.g., several seconds), before automatically presenting the next prompt in the series. For example, a patient may press the start control 906 once at the beginning of a training or calibration session, and each prompt may subsequently be presented by the BCI/assist device 102 without further action from the patient. The prompt may additionally/alternatively be presented until the prompted action has been performed by the user. For example, the prompt "Right" that is depicted in FIG. 9A may be presented until the BCI/assist device has detected that the patient has complied with the prompt. In another example, the patient may additionally control the presentation timing of each prompt in a series of prompts. For instance, a patient may press the start control 906 to instruct the BCI/assist device 102 to present a first prompt (e.g., after a short time delay), the patient may again press the start control 906 to instruct the BCI/assist device 102 to present a second prompt, and so forth. After presenting (automatically or under patient control) each prompt in a series of prompts, for example, the user interface 902*a* can update the progress indicator 908 to reflect the session's current progress.

Figure 9B:
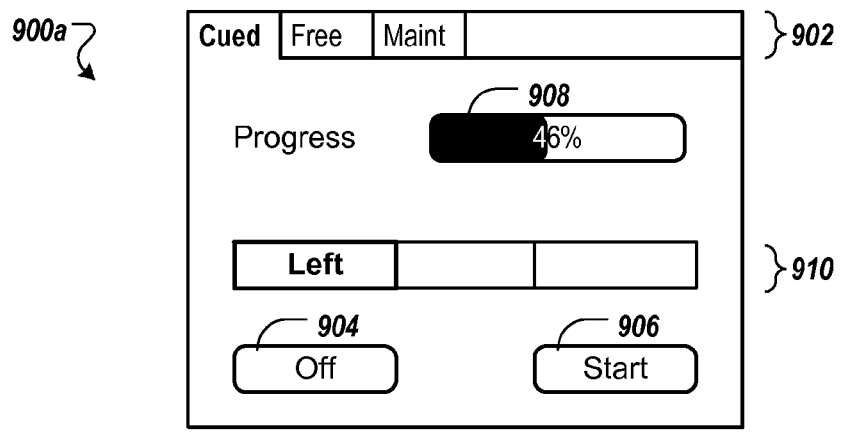
Figure 9C:
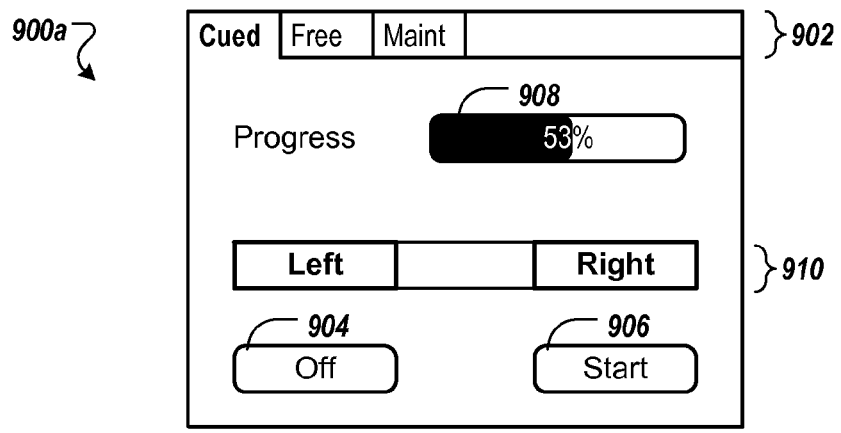

Prompt presentation may include descriptive and/or positional elements to instruct a patient to move particular body parts. As shown in FIG. 9A, for example, the BCI/assist device 102 can prompt the patient to move his or her right hand, by displaying the cue "right" on the right side of the prompt presentation area 910. Upon perceiving the prompted instruction, for example, the patient can begin moving his or her right hand, and can continue moving the hand while the instruction is displayed. As shown in FIG. 9B, for example, the patient may be prompted to move his or her left hand, by displaying the cue "left" on the left side of the prompt presentation area 910. Similar to the previous example, the patient can begin moving his or her left hand upon perceiving the prompted instruction, and can continue moving the hand while the instruction is displayed. As shown in FIG. 9C, for example, the patient may be prompted by the BCI/assist device 102 to move his or her left and right hands at the same time, by simultaneously displaying the cue "left" on the left side of the prompt presentation area 910 and the cue "right" on the right side of the prompt presentation area 910. Similar to both previous examples, the patient can begin simultaneously moving both of his or her hands upon perceiving the prompted instruction, and can continue moving the hands while the instruction is displayed. In general, by consistently presenting prompts at particular positions on the user interface 900*a* that are associated with body part movement (e.g., presenting a prompt on a left side of a screen to move a left hand), the prompts may be more quickly processed and performed by a patient. For instance, a patient may more quickly process positional differences between prompts than textual differences—meaning that a patient may understand and respond to positional prompts more quickly than mere textual prompts. Such decreased reaction time can allow for the brain signals that are responsive to the prompt to be more closely connected in time to the prompt, which can aid the BCI/assist device in reliably identifying features from brain signals that are associated with the prompted action.

Figure 9D:
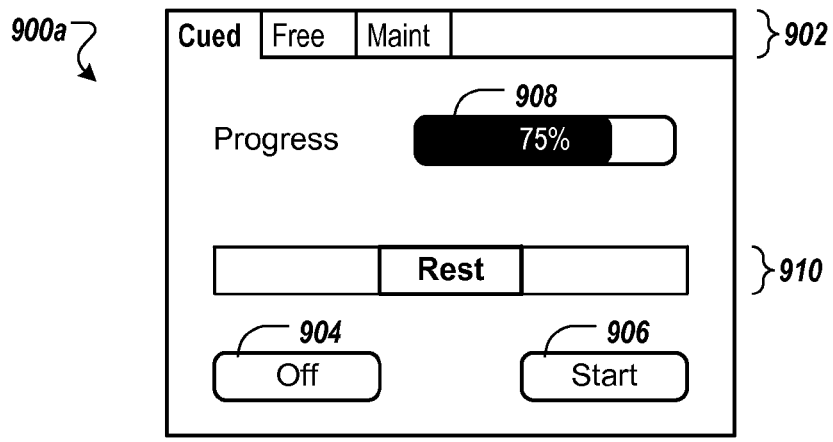

During a training mode (e.g., training mode 804) and/or calibration mode (calibration mode 810), patients may be periodically prompted to rest (e.g., to not move any part of the patient's body). Referring to FIG. 9D, for example, the prompt presentation area 910 can prompt a patient to rest by displaying the cue "rest" in the middle of the prompt presentation area 910. Prompts to rest may be interspersed between prompts which instruct the patient to perform an activity such as the movement of one or both hands, for example. Thus, the patient's brain signals may be allowed to return to a state associated with non-activity before prompting the patient to perform a different activity.

In some implementations, a subset of the prompts provided to a user (e.g., a patient) during a training session may be provided to the user during a calibration session. For example, a patient may be provided with prompts to move an impaired hand, to move an unimpaired hand, to move both hands, and to rest during a training session. During a calibration session, however, the patient may be provided with prompts to move only the impaired hand and to rest, for example.

Figure 9E:
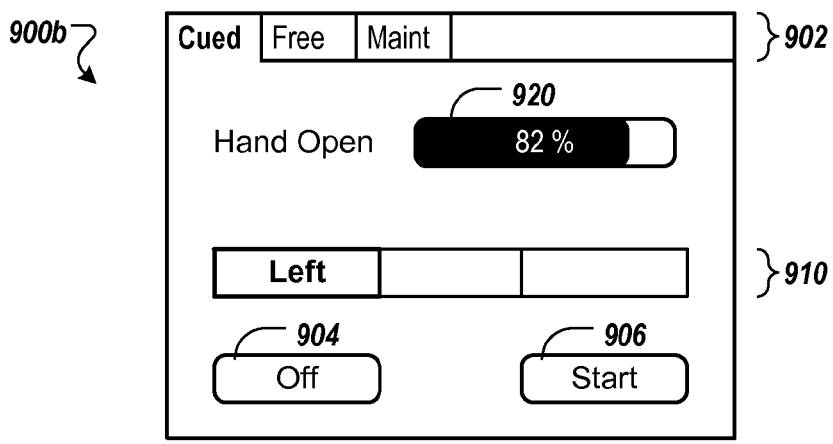
Figure 9F:
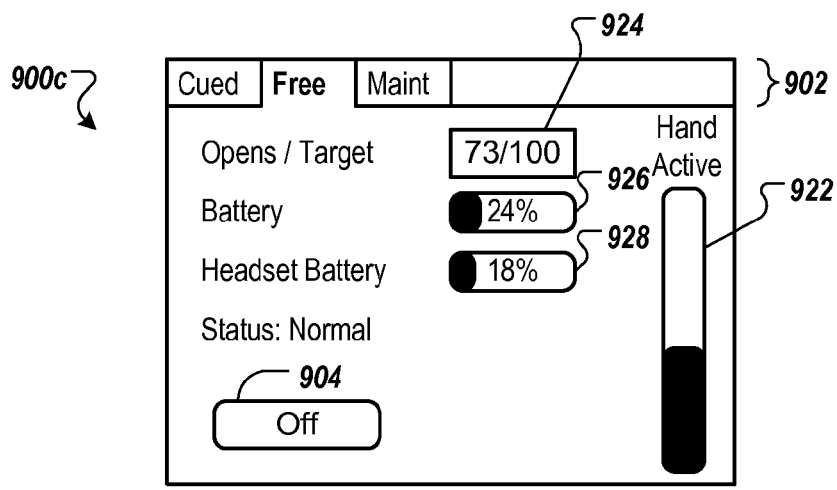

Referring now to FIGS. 9E and 9F, there are shown an example series of display screens of an instance of a graphical user interface (GUI) for prompting and/or providing feedback to a user (e.g., a patient) during a general operation mode (e.g., operation mode 806) process (e.g., the FIG. 8C method 840). User interfaces 900*b* and 900*c* may be visually presented to the user by display equipment included in a BCI/assist device. For example, the user interfaces 900*b* and 900*c* may be presented by the display device 106 of the BCI/assist device 102 (shown in FIG. 1), or by the visual output display equipment 206 of the BCI/assist device 202 (shown in FIG. 2).

In general, a patient can use a BCI/assist device in a general operation mode (e.g., operation mode 806) after completing a calibration session. During the general operation mode, for example, the patient may respond to prompts in a cued mode, or may choose to use the BCI/assist device as a robotic assistance device in a free control mode. Thus, therapy sessions can have variation, and the patient may have some flexibility in selecting a suitable therapy style.

Referring to FIG. 9E, the user interface 900b depicts an example GUI that can be used during cued operation mode (e.g., cued operation mode 807a) during which a patient is prompted to perform various actions. The user interface 900b includes the mode selection control 902. In the present example, the mode selection control 902 indicates that a BCI/assist device (e.g., the BCI/assist device 102) is in a cued operation mode. After performing a calibration session, for example, the BCI/assist device 102 may transition to a cued operation mode in which the patient is cued to alternately move and to rest an impaired body part. For example, the prompt presentation area 910 can prompt the patient to move his or her left hand. Information related to the patient's intention to move a body part (e.g., the left hand) may be presented to the patient by an intention indicator 920. For example, the intention indicator 920 may indicate a degree of agreement (i.e., matching) between the patient's current neural signals and neural signal data that have been previously correlated with a currently prompted action (e.g., a prompt to move the left hand). By viewing the intention indicator 920, for example, the patient may be aware of how his or her brain signals are currently being interpreted by the BCI/assist device 102.

In some implementations, the intention of a user to move a body part may be associated with a particular movement or action. For example, the body movement assistance component 108 of the BCI/assist device 102 may be placed in a closed hand position by default (e.g., at rest), and may be opened in response to a patient's intention to move the hand. As another example, the movement assistance component 108 may be placed in an open hand position by default (e.g., at rest), and may be closed in response to the patient's intention to move the hand. Based on the degree of agreement (i.e., matching) between the patient's current neural signals and stored neural signal data associated with body part movement, the intention indicator 920 may be updated, for example, while moving the movement assistance component 108.

Referring to FIG. 9F, the mode selection control 902 of the user interface 900c shows the BCI/assist device 102 in a free control mode (e.g., free control mode 807b). For example, the patient may select the control 902 to switch from the cued mode to the free control mode. While in free control mode, for example, the patient can use the BCI/assist device 102 to perform various tasks in his or her home, such as grasping objects. Similar to the intention indicator 920 of the user interface 900b, for example, the user interface 900c includes an intention indicator 922. The intention indicator 922, for example, may indicate a degree of agreement (i.e., matching) between the patient's current neural signals and neural signal data that have been previously correlated with a particular action (e.g., opening or closing an impaired hand). When the BCI/assist device 102 identifies the patient's current movement intention as corresponding to an action, for example, an activity counter indicator 924 (e.g., a total number of actions for a session relative to a target number of actions) can be incremented. Further, activity count information can be stored by the BCI/assist device 102 and can be provided to the central system 120.

Device status information can be provided to the patient through the user interface 900c. For example, a battery level indicator 926 and a headset battery indicator 928 can each be displayed during free control mode. Thus, the patient may recharge the BCI/assist device 102 and/or its associated brain signal acquisition system 112 (e.g., headset) when battery levels are low. Such device status information and/or activity count indicator 924 can also be presented in the other example user interfaces 900a and 900b.

Figure 9G:
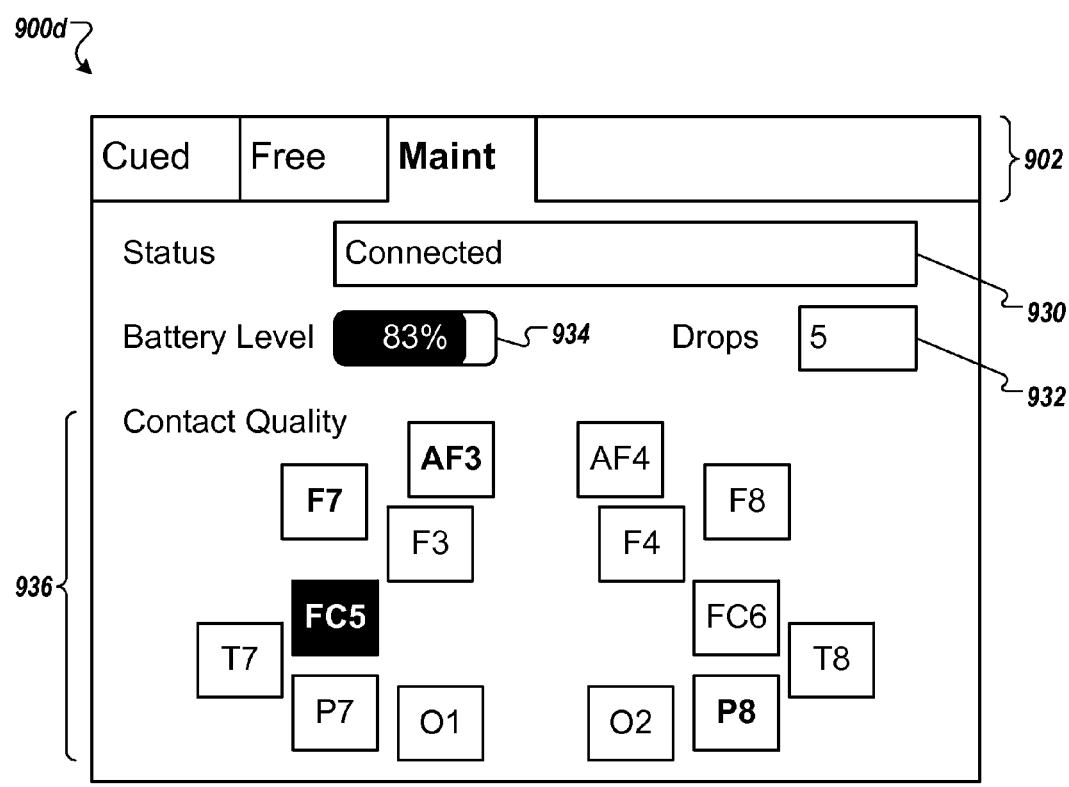

Referring now to FIG. 9G, an example display screen is shown of an instance of a graphical user interface (GUI) for providing device status and error information to a user. Similar to the previous user interfaces, for example, a user interface 900d may be visually presented to the user by display equipment included in a BCI/assist device. For example, the user interface 900d may be presented by the display device 106 of the BCI/assist device 102 (shown in FIG. 1), or by the visual output display equipment 206 of the BCI/assist device 202 (shown in FIG. 2).

In general, a user (e.g., a patient) can refer to the user interface 900d to troubleshoot possible issues with a BCI/assist device (e.g., the BCI/assist device 102) and/or its associated brain signal acquisition system (e.g., the signal acquisition system 112). For example, a connection between the BCI/assist device 102 and the signal acquisition system 112 (e.g., a headset) may be faulty, or one or more of the signal acquisition system's surface electrodes 114 may not be functioning correctly due to poor conductivity or some other issue.

The user interface 900d, for example, can include a connection status indicator 930 for indicating a current status of the connection between the BCI/assist device 102 and the signal acquisition system 112, and a connection drop indicator 932 for indicating a number of dropped connections during a current session. Further, the user interface 900d of the present example can include a battery level indicator 934 for indicating the current battery level of the BCI/assist device 102 and/or the signal acquisition system 112. Further, the user interface 900d of the present example can include a set of electrode contact quality indicators 936 for indicating a status of each of the individual electrodes of the brain signal acquisition system 112. Contact quality may be identified and differentiated by various visual indicators, such as color (e.g. green indicating good, yellow indicating fair, red indicating poor), font size, or some other type of indicator. Poorly operating electrodes may be identified and possibly remedied (e.g., by reapplying a contact gel) by the patient, for example. In the depicted example, a graphical icon associated with the electrode FC5 is highlighted, which can indicate that the BCI/assist device 102 is detecting a poor connection for this electrode on the signal acquisition system 112. In another example, the icons for electrodes F7, AF3, and P8 have bold text, which may indicate an intermediate quality connection for the corresponding electrodes on the signal acquisition system 112. The remaining icons may indicate a good quality connection for the corresponding electrodes in the signal acquisition system 112. The indicators 936 for the signal acquisition system 112 may be spatially arranged so as to correspond to the physical layout of the electrodes on the signal acquisition system 112. In another example, the indicators may be super-imposed over appropriate locations of an image/graphical depiction of the signal acquisition system 112, so as to help a patient quickly diagnose and resolve any connection problems.

Figure 10:
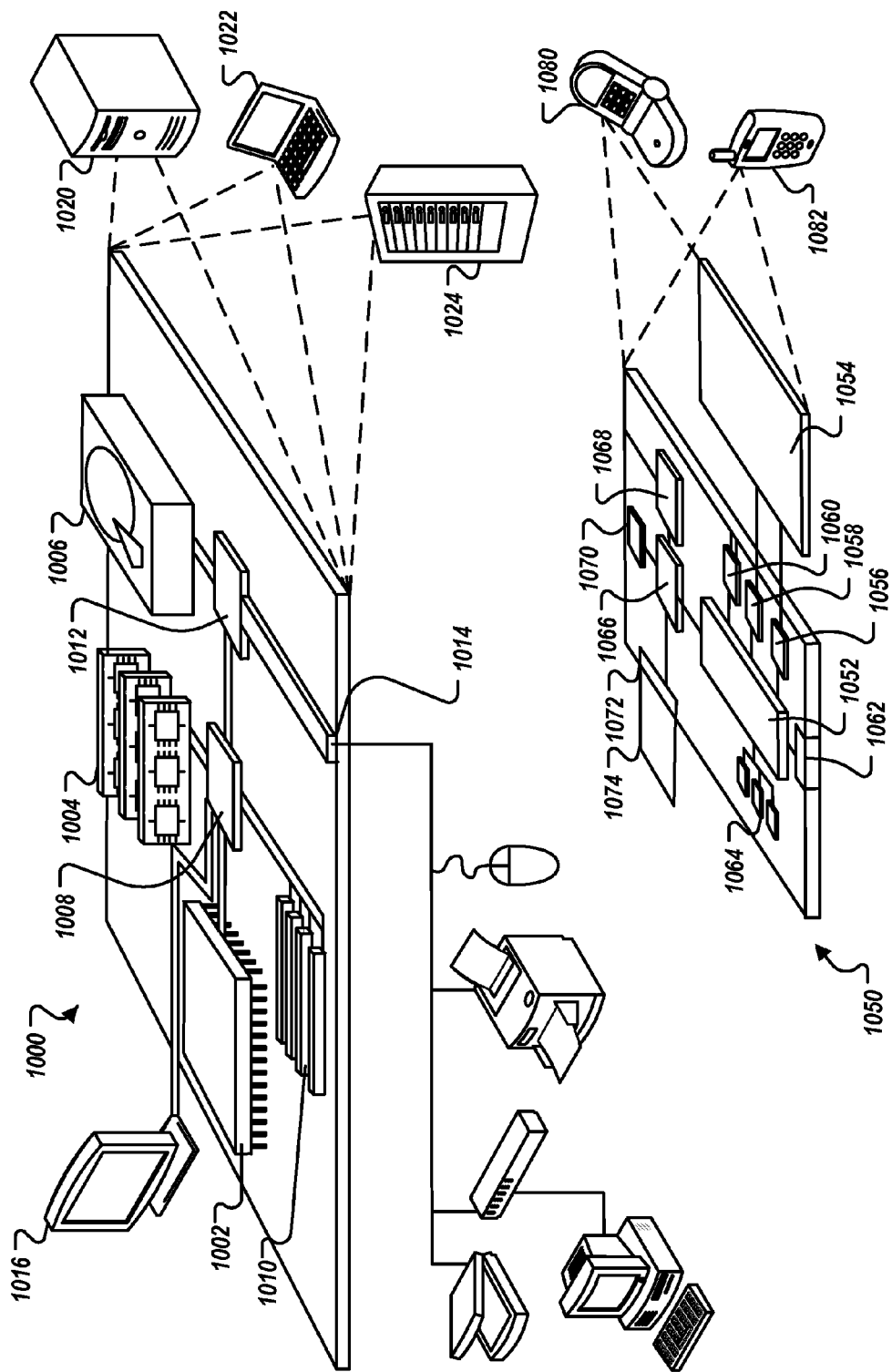
FIG. 10 shows an example of a generic computer device and a generic mobile computer device that may be used in connection with the devices and systems described in this specification.

FIG. 10 is a block diagram of computing devices 1000, 1050 that may be used to implement the systems and methods described in this document, as either a client or as a server or plurality of servers. Computing device 1000 is intended to represent various forms of digital computers, such as laptops, desktops, workstations, personal digital assistants, servers, blade servers, mainframes, and other appropriate computers. Computing device 1050 is intended to represent various forms of mobile devices, such as personal digital assistants, cellular telephones, smartphones, and other similar computing devices. Additionally computing device 1000 or 1050 can include Universal Serial Bus (USB) flash drives. The USB flash drives may store operating systems and other applications. The USB flash drives can include input/output components, such as a wireless transmitter or USB connector that may be inserted into a USB port of another computing device. The components shown here, their connections and relationships, and their functions, are meant to be exemplary only, and are not meant to limit implementations described and/or claimed in this document.

Computing device 1000 includes a processor 1002, memory 1004, a storage device 1006, a high-speed interface 1008 connecting to memory 1004 and high-speed expansion ports 1010, and a low speed interface 1012 connecting to low speed bus 1014 and storage device 1006. Each of the components 1002, 1004, 1006, 1008, 1010, and 1012, are interconnected using various busses, and may be mounted on a common motherboard or in other manners as appropriate. The processor 1002 can process instructions for execution within the computing device 1000, including instructions stored in the memory 1004 or on the storage device 1006 to display graphical information for a GUI on an external input/output device, such as display 1016 coupled to high speed interface 1008. In other implementations, multiple processors and/or multiple buses may be used, as appropriate, along with multiple memories and types of memory. Also, multiple computing devices 1000 may be connected, with each device providing portions of the necessary operations (e.g., as a server bank, a group of blade servers, or a multi-processor system).

The memory 1004 stores information within the computing device 1000. In one implementation, the memory 1004 is a volatile memory unit or units. In another implementation, the memory 1004 is a non-volatile memory unit or units. The memory 1004 may also be another form of computer-readable medium, such as a magnetic or optical disk.

The storage device 1006 is capable of providing mass storage for the computing device 1000. In one implementation, the storage device 1006 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The information carrier is a computer- or machine-readable medium, such as the memory 1004, the storage device 1006, or memory on processor 1002.

The high speed controller 1008 manages bandwidth-intensive operations for the computing device 1000, while the low speed controller 1012 manages lower bandwidth-intensive operations. Such allocation of functions is exemplary only. In one implementation, the high-speed controller 1008 is coupled to memory 1004, display 1016 (e.g., through a graphics processor or accelerator), and to high-speed expansion ports 1010, which may accept various expansion cards (not shown). In the implementation, low-speed controller 1012 is coupled to storage device 1006 and low-speed expansion port 1014. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 1000 may be implemented in a number of different forms, as shown in the figure. For example, it may be implemented as a standard server 1020, or multiple times in a group of such servers. It may also be implemented as part of a rack server system 1024. In addition, it may be implemented in a personal computer such as a laptop computer 1022. Alternatively, components from computing device 1000 may be combined with other components in a mobile device (not shown), such as device 1050. Each of such devices may contain one or more of computing device 1000, 1050, and an entire system may be made up of multiple computing devices 1000, 1050 communicating with each other.

Computing device 1050 includes a processor 1052, memory 1064, an input/output device such as a display 1054, a communication interface 1066, and a transceiver 1068, among other components. The device 1050 may also be provided with a storage device, such as a microdrive or other device, to provide additional storage. Each of the components 1050, 1052, 1064, 1054, 1066, and 1068, are interconnected using various buses, and several of the components may be mounted on a common motherboard or in other manners as appropriate.

The processor 1052 can execute instructions within the computing device 1050, including instructions stored in the memory 1064. The processor may be implemented as a chipset of chips that include separate and multiple analog and digital processors. Additionally, the processor may be implemented using any of a number of architectures. For example, the processor 1052 may be a CISC (Complex Instruction Set Computers) processor, a RISC (Reduced Instruction Set Computer) processor, or a MISC (Minimal Instruction Set Computer) processor. The processor may provide, for example, for coordination of the other components of the device 1050, such as control of user interfaces, applications run by device 1050, and wireless communication by device 1050.

Processor 1052 may communicate with a user through control interface 1058 and display interface 1056 coupled to a display 1054. The display 1054 may be, for example, a TFT (Thin-Film-Transistor Liquid Crystal Display) display or an OLED (Organic Light Emitting Diode) display, or other appropriate display technology. The display interface 1056 may comprise appropriate circuitry for driving the display 1054 to present graphical and other information to a user. The control interface 1058 may receive commands from a user and convert them for submission to the processor 1052. In addition, an external interface 1062 may be provide in communication with processor 1052, so as to enable near area communication of device 1050 with other devices. External interface 1062 may provide, for example, for wired communication in some implementations, or for wireless communication in other implementations, and multiple interfaces may also be used.

The memory 1064 stores information within the computing device 1050. The memory 1064 can be implemented as one or more of a computer-readable medium or media, a volatile memory unit or units, or a non-volatile memory unit or units. Expansion memory 1074 may also be provided and connected to device 1050 through expansion interface 1072, which may include, for example, a SIMM (Single In Line Memory Module) card interface. Such expansion memory 1074 may provide extra storage space for device 1050, or may also store applications or other information for device 1050. Specifically, expansion memory 1074 may include instructions to carry out or supplement the processes described above, and may include secure information also. Thus, for example, expansion memory 1074 may be provide as a security module for device 1050, and may be programmed with instructions that permit secure use of device 1050. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 1064, expansion memory 1074, or memory on processor 1052 that may be received, for example, over transceiver 1068 or external interface 1062.

Device 1050 may communicate wirelessly through communication interface 1066, which may include digital signal processing circuitry where necessary. Communication interface 1066 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 1068. In addition, short-range communication may occur, such as using a Bluetooth, WiFi, or other such transceiver (not shown). In addition, GPS (Global Positioning System) receiver module 1070 may provide additional navigation- and location-related wireless data to device 1050, which may be used as appropriate by applications running on device 1050.

Device 1050 may also communicate audibly using audio codec 1060, which may receive spoken information from a user and convert it to usable digital information. Audio codec 1060 may likewise generate audible sound for a user, such as through a speaker, e.g., in a handset of device 1050. Such sound may include sound from voice telephone calls, may include recorded sound (e.g., voice messages, music files, etc.) and may also include sound generated by applications operating on device 1050.

The computing device 1050 may be implemented in a number of different forms, as shown in the figure. For example, it may be implemented as a cellular telephone 1080. It may also be implemented as part of a smartphone 1082, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), peer-to-peer networks (having ad-hoc or static members), grid computing infrastructures, and the Internet.

The computing system may include clients and servers. A client and server are generally remote from each other and typically interact through a communication network. The relationship of client and server arises by virtue of computer programs running on the respective computers and having a client-server relationship to each other.

A number of embodiments have been described. Nevertheless, it will be understood that various modifications may be made without departing from the spirit and scope of the invention. In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the following claims.

What is claimed is:

1. A body worn brain-controlled body movement assistance device, the device comprising:
    a body worn brain-computer interface (BCI) component adapted to be mounted to a user, the BCI component configured to (i) receive brain signal information captured from the user by a brain signal acquisition system, (ii) process the captured brain signal information to detect if the captured brain signal information is indicative of an intention by the user related to one or more predefined movements of one or more of the user's body parts, and (iii) when an intention of one of the one or more predefined movements is detected, produce an output signal indicative of a detected predefined movement;

a body movement assistance component operably connected to the BCI component and adapted to be worn by the user in proximity to and attached with the body parts of the one or more predefined movements, the body movement assistance component being configured to (i) receive from the BCI component the output signal indicative of the detected predefined movement, and (ii) in response thereto, induce or assist in moving the one or more body parts in accordance with the detected predefined movement; and a prompt mechanism operably connected to the BCI component, the prompt mechanism comprising a display device configured to display information generated by the BCI component to prompt the user to attempt finger movements, wherein the body worn brain-controlled body movement assistance device is portable by virtue of the BCI component, the body movement assistance component, and the display device each being wearable on an upper limb of the user, and wherein the BCI component, the body movement assistance component, and the display device are each located in a single body worn brain-controlled body movement assistance device adapted to be worn on the upper limb of the user in such a way that the user is able to ambulate freely while wearing the device.

2. The body-worn brain-controlled body movement assistance device of claim 1, wherein the display device is adapted to be on the forearm of the user to enable the user to view the display device while the user is utilizing the body worn brain-controlled movement assistance device.

3. The body-worn brain-controlled body movement assistance device of claim 1, wherein the prompt mechanism comprises one or more tactile prompt interfaces that are configured to provide tactile stimulation to one or more portions of the user's body.

4. The born-worn brain-controlled body movement assistance device of claim 1, wherein the prompt mechanism comprises one or more electrical stimulators that are configured to stimulate particular nerves or muscles of the user's body through the application of electrical current at one or more locations on the user's body.

5. The born-worn brain-controlled body movement assistance device of claim 1, wherein the prompt mechanism comprises an audio output device that is configured to audibly output information to prompt the user to attempt the finger movements.

6. The body-worn brain-controlled body movement assistance device of claim 2, wherein the prompt mechanism is configured to output information relating to a usage session of the body-worn brain-controlled body movement assistance device on the display device.

7. The body-worn brain-controlled body movement assistance device of claim 6, wherein the BCI component is configured to wirelessly receive the brain signal information captured from the user by the brain signal acquisition system.

8. The body-worn brain-controlled body movement assistance device of claim 7, wherein the usage session of the body-worn brain-controlled body movement assistance device comprises a rehabilitation session during which one or more rehabilitation exercises are performed by the body movement assistance component with regard to one or more fingers of the user based on captured brain signals that are determined by the BCI interface to indicate an intention to move the one or more fingers.

9. The body-worn brain-controlled body movement assistance device of claim 1, wherein the body-worn brain-controlled body movement assistance device is configured to operate in a training mode during which (i) the prompt mechanism generates a particular prompt to the user, (ii) the BCI component captures particular brain signal information of the user resulting from an intention by the user to make one or more body part movements in response to the particular prompt, and (iii) identifies a correlation between the particular brain signal information and the intention by the user to make one or more body part movements.

10. The body-worn brain-controlled body movement assistance device of claim 1, wherein the body-worn brain-controlled body movement assistance device is configured to operate in a cued mode during which (i) the prompt mechanism generates one or more particular prompts to the user and (ii) the body movement assistance component induces or assists movement of one or more particular body parts of the user in accordance with the one or more particular prompts.

11. The body-worn brain-controlled body movement assistance device of claim 10, wherein the one or more particular prompts are dynamically determined by the BCI component based on the user's prior rehabilitation session performance or a prescribed therapy schedule for the user.

12. The body-worn brain-controlled body movement assistance device of claim 1, wherein the body-worn brain-controlled body movement assistance device is configured to operate in a free mode during which the body movement assistance component induces or assists a particular movement of one or more particular body parts of the user in response to the BCI component receiving particular brain signal information that the BCI component correlates to the particular movement of the one or more particular body parts of the user.

13. The body-worn brain-controlled body movement assistance device of claim 1, wherein the BCI component includes a housing located in the body-worn brain-controlled body movement assistance device such that the housing adapted to be worn on a forearm of the user.

14. The body-worn brain-controlled body movement assistance device of claim 13, wherein the display device is located on the housing and positioned on a top of the housing such that the user can readily view the display device while wearing the housing on the forearm.

15. The body-worn brain-controlled body movement assistance device of claim 1, wherein the body movement assistance component is configured to be worn on one or more fingers of the user.

16. The body-worn brain-controlled body movement assistance device of claim 1, wherein the body movement assistance component is operably connected to the BCI component by hardwiring disposed between the body movement assistance component and the BCI component.

* * * * *

UNITED STATES PATENT AND TRADEMARK OFFICE
CERTIFICATE OF CORRECTION

PATENT NO.         : 9,539,118 B2
APPLICATION NO.    : 13/842749
DATED              : January 10, 2017
INVENTOR(S)        : Eric C. Leuthardt et al.

It is certified that error appears in the above-identified patent and that said Letters Patent is hereby corrected as shown below:

In the Claims

Column 41, Line 22 (approx.), Claim 1, before "being" delete "each";

Column 41, Lines 31-32 (approx.), Claim 2, before "adapted" delete "is";

Column 41, Line 32 (approx.), Claim 2, please delete "on the" and insert -- positioned on a --, therefor;

Column 41, Line 40 (approx.), Claim 4, please delete "born-" and insert -- body --, therefor;

Column 41, Line 46 (approx.), Claim 5, please delete "born-" and insert -- body --, therefor.

Signed and Sealed this
Fourth Day of July, 2017

Joseph Matal
*Performing the Functions and Duties of the*
*Under Secretary of Commerce for Intellectual Property and*
*Director of the United States Patent and Trademark Office*